US012766130B2

(12) United States Patent
Min et al.

(10) Patent No.: US 12,766,130 B2
(45) Date of Patent: Oct. 20, 2026

(54) PHARMACEUTICAL COMPOSITION OF (S)-KETOROLAC AND PREPARATION METHOD THEREFOR

(71) Applicant: NANJING HERON PHARMACEUTICAL SCIENCE AND TECHNOLOGY CO., LTD., Nanjing (CN)

(72) Inventors: Tao Min, Nanjing (CN); Wenliang Zhou, Nanjing (CN); Jialin Wang, Nanjing (CN); Hai Ye, Nanjing (CN); Ying Xu, Nanjing (CN); Meiling Mo, Nanjing (CN); Si Li, Nanjing (CN); Ye Xu, Nanjing (CN)

(73) Assignee: NANJING HERON PHARMACEUTICAL SCIENCE AND TECHNOLOGY CO., LTD., Nanjing (CN)

( * ) Notice: Subject to any disclaimer, the term of this patent is extended or adjusted under 35 U.S.C. 154(b) by 1156 days.

(21) Appl. No.: 17/776,428

(22) PCT Filed: Sep. 17, 2021

(86) PCT No.: PCT/CN2021/118953

§ 371 (c)(1),
(2) Date: May 12, 2022

(87) PCT Pub. No.: WO2022/241983

PCT Pub. Date: Nov. 24, 2022

(65) Prior Publication Data

US 2024/0173296 A1 May 30, 2024

(30) Foreign Application Priority Data

May 18, 2021 (CN) ........................ 202110537672.6

(51) Int. Cl.

| | |
|---|---|
| ***A61K 31/407*** | (2006.01) |
| ***A61K 9/00*** | (2006.01) |
| ***A61K 9/19*** | (2006.01) |
| ***A61K 47/02*** | (2006.01) |
| ***A61K 47/12*** | (2006.01) |
| ***A61K 47/18*** | (2017.01) |
| ***A61K 47/26*** | (2006.01) |
| ***A61K 47/36*** | (2006.01) |

(52) U.S. Cl.

CPC .......... *A61K 31/407* (2013.01); *A61K 9/0019* (2013.01); *A61K 9/19* (2013.01); *A61K 47/02* (2013.01); *A61K 47/12* (2013.01); *A61K 47/18* (2013.01); *A61K 47/183* (2013.01); *A61K 47/26* (2013.01); *A61K 47/36* (2013.01)

(58) Field of Classification Search

CPC .................................................... A61K 31/407

See application file for complete search history.

(56) References Cited

U.S. PATENT DOCUMENTS

2021/0069151 A1 3/2021 Del Carmen Garcia Armenta

FOREIGN PATENT DOCUMENTS

| | | | | |
|---|---|---|---|---|
| CN | 101167722 A | 4/2008 | | |
| CN | 102138891 A | 8/2011 | | |
| CN | 103167800 A | 6/2013 | | |
| CN | 108289859 A | 7/2018 | | |
| CN | 110540542 A | 12/2019 | | |
| CN | 111454271 A | 7/2020 | | |
| EP | 3818981 A1 | 5/2021 | | |
| MX | 2013005378 A | 11/2014 | | |
| WO | WO-2008115572 A1 * | 9/2008 | .......... | A61K 9/0019 |

OTHER PUBLICATIONS

Chinese Office Action for CN Application No. 202110537672.6, including English translation, 19 pages, dated Jul. 5, 2022.

International Search Report for PCT/CN2021/118953, 7 pages, dated Feb. 11, 2022.

* cited by examiner

*Primary Examiner* — John S Kenyon

(74) *Attorney, Agent, or Firm* — Kilpatrick Townsend & Stockton LLP

(57) ABSTRACT

Provided are a pharmaceutical composition of (S)-ketorolac and a preparation method therefor, which belong to the technical field of pharmaceutical preparations. The pharmaceutical composition includes (S)-ketorolac or a pharmaceutically acceptable salt thereof, a stabilizer, a pH-adjusting agent, and an excipient, and the dosage form of the pharmaceutical composition is preferably lyophilized powder injection. The lyophilized powder injection prepared herein has optical purity of an active ingredient greater than or equal to 95% after being stored under long-term stability test conditions for 6 months and optical purity of an active ingredient greater than or equal to 90% after being stored under accelerated stability test conditions for 6 months. The lyophilized powder injection has important use in the preparation of non-steroidal anti-inflammatory drugs with analgesic, anti-inflammatory, antipyretic effects.

19 Claims, 4 Drawing Sheets

Integration Results

| No. | Retention (DETECTED) min | Area mAU*min | Rel.Area % | Height mAU | Plates (EP) | Asymmetry (EP) | Resolution (USP |
|---|---|---|---|---|---|---|---|
| 1 | 11.393 | 1.202 | 0.58 | 2.247 | 3191 | 1.16 | n.a. |
| 2 | 14.567 | 204.428 | 99.42 | 241.547 | 2152 | 1.84 | 2.97 |
| Total: | | | 100.000 | 243.793 | 5343.00 | 2.99 | |

Integration Results

| No. | Retention (DETECTED) min | Area mAU*min | Rel.Area % | Height mAU | Plates (EP) | Asymmetry (EP) | Resolution (USP |
|---|---|---|---|---|---|---|---|
| 1 | 11.380 | 2.268 | 1.32 | 4.237 | 3207 | 1.18 | n.a. |
| 2 | 14.583 | 169.178 | 98.68 | 204.628 | 2288 | 1.76 | 3.11 |
| Total: | | | 100.000 | 208.865 | 5495.00 | 2.94 | |

PHARMACEUTICAL COMPOSITION OF (S)-KETOROLAC AND PREPARATION METHOD THEREFOR

CROSS-REFERENCE TO RELATED APPLICATION(S)

This application claims priority to Chinese Patent Application No. 202110537672.6 filed with the China National Intellectual Property Administration (CNIPA) on May 18, 2021.

TECHNICAL FIELD

The present application belongs to the technical field of pharmaceutical preparations and in particular, relates to a pharmaceutical composition of (S)-ketorolac and a preparation method therefor.

BACKGROUND

Ketorolac tromethamine is a non-steroidal antipyretic-analgesic drug with a special structure of piromidic acid derivatives, which was first developed and marketed by SYNTEX LABORATORIES, INC., US. It obtains analgesic, anti-inflammatory and antipyretic effects by inhibition of prostaglandin (PG) synthesis instead of acting on opioid receptors or stimulation of the release of opioid peptides in vivo. Ketorolac tromethamine can relieve moderate pain of various muscles, soft tissues and joints, is suitable for short-term treatment of acute and severe pain requiring opioid analgesics, is usually used for postoperative analgesia, but is not suitable for the treatment of mild or chronic pain, and is non-addictive. In the standard animal model of analgesic activity, the analgesic activity of ketorolac tromethamine is 800 times that of Aspirin, much stronger than that of Indomethacin and Naproxen, and superior to that of Phenylbutazone. Compared with opioid analgesics, ketorolac has the advantages of quick onset and long action time, and has no addiction, central nervous system damage, respiratory depression, constipation or other adverse effects. The combination of ketorolac and morphine can reduce the dosage of morphine and reduce the adverse effects and addiction caused by morphine.

At present, the main dosage forms of ketorolac tromethamine used clinically in China are tablets, capsules, injections and eye drops. Nasal sprays are also approved in the United States. In addition, the external preparations of ketorolac, such as gels, have gradually attracted the attention of researchers.

Ketorolac tromethamine injection has been widely used in clinical postoperative analgesia and other fields because of its rapid analgesic effect. At present, there are two main formulations of ketorolac tromethamine injection appearing on the market at home and abroad: one is a formulation with potassium dihydrogen phosphate as pH-adjusting agents, represented by the products of YUNG SHIN PHARM. IND. (KUNSHAN) CO., LTD.; and the other is a formulation with ethanol as a stabilizer, used by most companies. However, the conventional formulations of ketorolac tromethamine injection contain ethanol as a cosolvent and a stabilizer. During long-term storage, with the inevitable volatility of ethanol, there are still white spots or crystals precipitated, affecting the quality indexes such as visible particles and insoluble particles and causing potential safety hazards in clinical use. In addition, in combination with cephalosporin antibiotics, disulfiram reaction can occur, which leads to blood pressure drop, heartbeat acceleration or electrocardiogram partial change. Therefore, ketorolac tromethamine injection containing ethanol has potential safety hazards.

Chinese patent CN101199514A improves the clarity of ketorolac tromethamine injection by adding 10% to 60% of propylene glycol to the conventional formulation, and also improves the white spots after sterilization. However, since propylene glycol solvent is used in the preparation, the adverse stimulation caused by the current use of propylene glycol still cannot be avoided, which is not beneficial to the popularization and application of drugs, and the related substances increase rapidly.

Chinese patent CN102846542A improves the clarity of injection after storage by adding glycerol to the formulation and also hopes to improve the clarity and storage stability of injection by adding poloxamer 188. However, since cholesterol, oleic acid, sodium oleate, glycerol or poloxamer 188 is selected as a stabilizer, among which cholesterol and oleic acid are prone to be oxidized and poloxamer, as a surfactant, has certain hemolysis and sensitization, the injection has the risk of hemolysis and sensitization, which easily leads to safety problems.

The active pharmaceutical ingredients reported in the approved preparations and public literature are all ketorolac tromethamine whose acid radical ketorolac is racemate, which is composed of (S)-ketorolac and (R)-ketorolac in equal quantities. Ketorolac can easily cause serious adverse effects such as systemic anaphylaxis, gastrointestinal perforation, gastric bleeding, asthma, pulmonary edema, kidney failure, etc., and these serious side effects limit the dosage and medication time of ketorolac in pain treatment. (S)-ketorolac, as an effective single isomer, can reduce the renal metabolic burden caused by (R)-ketorolac having no analgesic effect, which may be a development exploration to reduce adverse effects.

The optical rotation of (S)-ketorolac is negative, its stereo configuration is an S-enantiomer, and its structure is as shown by the compound of Formula I. (S)-ketorolac exerts the main analgesic effect. The optical rotation of (R)-ketorolac is positive, and its stereo configuration is R-enantiomer. (R)-ketorolac hardly has analgesic effect, which may be one of the reasons for lots of adverse effects caused by ketorolac. The structure of (R)-ketorolac is as follows. Seeking and developing single isomer drugs of ketorolac has attracted more and more attention of researchers.

Compound of Formula I

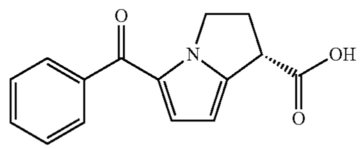

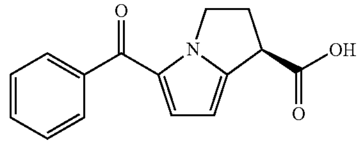

(R)-ketorolac

Studies have shown that the efficacy of (S)-ketorolac is much stronger than that of (R)-ketorolac. The analgesic effect of (S)-ketorolac is 230 times that of (R)-ketorolac, and the anti-inflammatory effect of (S)-ketorolac is 60 times that of (R)-ketorolac. Therefore, if a single S-isomer is used for administration, the dosage can be reduced by nearly half compared with racemate administration under the condition of producing the same efficacy, thereby reducing the toxic and side effects. Therefore, it is meaningful to obtain optically active S-isomers. The conversion between (S)-ketorolac and (R)-ketorolac occurs in mice and rats in different degrees, while the conversion ratio from (S)-ketorolac to (R)-ketorolac in the human body is less than or equal to 6.5% (see literature J Cln Pharmacol 1996; 36:521-539). The preparation of single (S)-ketorolac has the advantages of lower dosage, better curative effect and higher safety and has broad development prospects.

Ketorolac has a unique chemical structure, that is, a pyrrolopyrrolidine heterocyclic ring, which is different from the structure of the common aryl propionic acid non-steroidal anti-inflammatory drugs such as ibuprofen. The chiral center of (S)-ketorolac is located on this special pyrrolopyrrolidine heterocyclic ring, which leads to the racemization of the molecules when the temperature rises, especially when the molecules are in a solution state, and more isomer impurities of (R)-ketorolac are produced.

Chinese patent CN108451909A reports that "ketorolac tromethamine is unstable to light, heat, acid and alkali, and it is prone to decarboxylation and oxidation reaction to produce impurities, to a certain extent, affecting the safety of clinical medication". Gu et al. (International Journal of Pharmaceutics, 1988, 41, 105-113) report that ketorolac tromethamine produces an oxidized intermediate (originally labeled as Impurity 2) by photolysis of free radicals under illumination, and further produces 1-keto ketorolac (originally labeled as Impurity 3) and 1-hydroxy ketorolac (originally labeled as Impurity 1). The structures of related compounds are as follows.

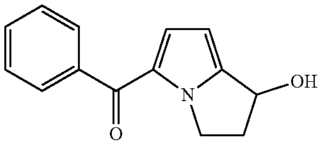

1-hydroxy ketorolac

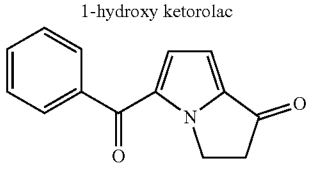

1-keto ketorolac

There are no reports and teachings on how to maintain optical stability in (S)-ketorolac injection in the existing public literature. Through literature review and experimental exploration, we found that it is difficult to maintain the chiral optical purity of the active pharmaceutical ingredient in the preparation of (S)-ketorolac. Therefore, how to maintain the optical stability of (S)-ketorolac in preparations by means of preparation technology is a challenging issue, which needs to be solved urgently.

SUMMARY

The present application provides a pharmaceutical composition of (S)-ketorolac and a preparation method therefor. (S)-ketorolac is an active optical isomer exerting drug efficacy in ketorolac tromethamine. The separation of (S)-ketorolac from the racemate to make (S)-ketorolac preparations is beneficial to the improvement of the efficacy per dose administered and reduce the obvious adverse effects of ketorolac tromethamine and has broad clinical application prospects.

In a first aspect, the present application provides a pharmaceutical composition of (S)-ketorolac. The pharmaceutical composition includes: (1) a compound of Formula I, namely (S)-ketorolac or a pharmaceutically acceptable salt or a solvate thereof; (2) a pH-adjusting agent; and (3) a pharmaceutically acceptable excipient. The chemical structure of (S)-ketorolac is as shown in the compound of Formula I:

Compound of Formula I

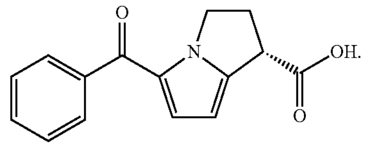

In the pharmaceutical composition of the present application, the pharmaceutically acceptable salt is selected from one or more of (S)-ketorolac sodium salt, (S)-ketorolac tromethamine salt, (S)-ketorolac diethylamine slat, (S)-ketorolac ethylenediamine salt, (S)-ketorolac lysine salt, (S)-ketorolac arginine salt, (S)-ketorolac histidine salt or (S)-ketorolac meglumine salt.

The pharmaceutical composition of the present application is in a dosage form of lyophilized powder injection, solution injection, or sterile powder in which various components are uniformly mixed.

The pharmaceutical composition of the present application is preferably lyophilized powder injection, and the lyophilized powder injection has optical purity of an active ingredient greater than or equal to 95% in the long-term stability test, that is, after being stored under conditions of 25° C.±2° C./60% RH±5% RH for 6 months, and optical purity of an active ingredient greater than or equal to 90% in the accelerated stability test, that is, after being stored under conditions of 10 40° C.±2° C./75% RH±5% RH for 6 months; and a moisture content of the lyophilized powder injection is less than or equal to 5%, preferably less than or equal to 3%, and more preferably less than or equal to 2%.

In a preferred embodiment of the present application, an active pharmaceutical ingredient (API) used in the preparation is selected from (S)-ketorolac, (S)-ketorolac sodium salt, (S)-ketorolac tromethamine salt, (S)-ketorolac diethylamine slat, (S)-ketorolac ethylenediamine salt, (S)-ketorolac lysine salt, (S)-ketorolac arginine salt, (S)-ketorolac histidine salt, and (S)-ketorolac meglumine salt.

The pH-adjusting agent includes two parts: a buffer and a certain-volume pH-adjusting agent. The buffer is anhydrous or crystalline water-containing phosphate and a solution thereof, acetate and a solution thereof, citrate and a solution thereof, a triethylamine buffer solution, a borax buffer solution, or a mixture thereof, preferably phosphate and a solution thereof, acetate and a solution thereof, or citrate and a solution thereof, where the anhydrous or crystalline water-containing phosphate is selected from one or more of sodium dihydrogen phosphate, disodium hydrogen phosphate, potassium dihydrogen phosphate, dipotassium hydrogen phosphate, sodium phosphate, tripotassium phosphate, sodium hydrogen phosphate, potassium hydrogen phosphate, ammonium hydrogen phosphate, ammonium dihydrogen phosphate, ammonium phosphate, calcium dihydrogen phosphate, calcium hydrogen phosphate or zinc phosphate.

The certain-volume pH-adjusting agent is selected from sodium hydroxide, potassium hydroxide, tromethamine, triethanolamine, diethanolamine, ethanolamine, sodium citrate, potassium citrate, sodium carbonate, sodium bicarbonate, anhydrous or crystalline hydrate of disodium hydrogen phosphate, anhydrous or crystalline hydrate of sodium dihydrogen phosphate, anhydrous or crystalline hydrate of dipotassium hydrogen phosphate, anhydrous or crystalline hydrate of potassium dihydrogen phosphate, sodium phosphate, phosphoric acid, hydrochloric acid, tartaric acid or lactic acid, preferably anhydrous or crystalline hydrate of disodium hydrogen phosphate, anhydrous or crystalline hydrate of sodium dihydrogen phosphate, phosphoric acid, or an aqueous solution prepared from the same.

The excipient is selected from mannitol, dextran, sucrose, maltose, lactose, glycine, maltodextrin or povidone K30, preferably mannitol or maltodextrin. In the present application, mannitol or/and maltodextrin are preferred as the lyophilized excipient, and compared with other excipients, mannitol or/and maltodextrin have the most stable compatibility and the best application effect.

In a preferred embodiment of the present application, the certain-volume pH-adjusting agent is used for regulating a pH value of a lyophilized stock solution when the lyophilized powder injection is prepared to be 6.5 to 7.5, preferably 6.8 to 7.2, and more preferably 6.9 to 7.0.

In a preferred embodiment of the present application, a drug concentration of (S)-ketorolac $C_{15}H_{13}NO_3$ in the lyophilized stock solution when the lyophilized powder injection is prepared is 2 mg/ml to 30 mg/ml, preferably 5 mg/ml to 10 mg/ml.

The pharmaceutical composition obtained in the present application may also be diluted with a diluent for use. Preferably, the lyophilized powder injection may be diluted with a clinically commonly used diluent for use. The diluent is selected from 5% glucose injection, 10% glucose injection, glucose sodium chloride injection, 0.9% sodium chloride injection, compound sodium chloride injection, sodium lactate Ringer's injection, compound glucose sodium lactate injection, sterilized water for injection, xylitol injection or fructose injection. The concentration of (S)-ketorolac $C_{15}H_{13}NO_3$ is 0.05 mg/ml to 5 mg/ml after dilution.

In a preferred embodiment of the present application, in the lyophilized powder injection, the active pharmaceutical ingredient is selected from (S)-ketorolac, (S)-ketorolac tromethamine salt or (S)-ketorolac arginine salt; in the pH-adjusting agent, the buffer is selected anhydrous or crystalline water-containing phosphate, and for example, may be one or more of anhydrous or crystalline water disodium hydrogen phosphate, or anhydrous or crystalline water sodium dihydrogen phosphate; the certain-volume pH-adjusting agent is selected from anhydrous or crystalline water disodium hydrogen phosphate, anhydrous or crystalline water sodium dihydrogen phosphate, phosphoric acid, sodium hydroxide, or an aqueous solution prepared from the same; the excipient is selected from mannitol; and the drug concentration of (S)-ketorolac in the lyophilized stock solution when the lyophilized powder injection is prepared is 5 mg/ml to 7.5 mg/ml, and the pH value of the lyophilized stock solution before lyophilizing is 6.8 to 7.2

The active pharmaceutical ingredient used in the preparation of the present application, for example, (S)-ketorolac, is solid powder with a color form off-white to light yellow and is nearly or completely insoluble in water, slightly soluble in dichloromethane, sparingly soluble in anhydrous ethanol, soluble in methanol, and freely soluble in dimethylformamide.

Through physical and chemical experiments, the solubility of (S)-ketorolac is pH-dependent, and its solubility increases with the increase of pH. Under acidic conditions, when the pH value is below 6.0, it is not beneficial to the dissolution of active ingredient (S)-ketorolac, and the formability and reconstitution effect of prepared products are poor; when the pH value is above 6.8, (S)-ketorolac has higher solubility; when the pH value is in the range of 6.0 to 7.5, with the increase of pH, the rate of (S)-ketorolac performing conformational inversion to form (R)-ketorolac is very low, indicating that the optical stability of (S)-ketorolac lyophilized preparation is better; and when the pH value is greater than 7.5, the rate of (S)-ketorolac performing conformational inversion to form (R)-ketorolac increases, the content of (R)-ketorolac in the lyophilized preparation increases, and the optical stability of reconstitution solution decreases.

In a preferred embodiment of the present application, a molar concentration of phosphate used as the pH-adjusting agent in the lyophilized powder injection is 0.01 mmol/ml to 0.1 mmol/ml, preferably 0.05 mmol/ml to 0.06 mmol/ml; a molar ratio of (S)-ketorolac to phosphate in the lyophilized stock solution is 1:1 to 1:3, preferably 1:2.5 to 1:2.8; and a mass percentage of the excipient mannitol in the lyophilized stock solution is 3% to 7%, preferably 5%.

The examination of visible particles and insoluble particles is an important item in the quality control of lyophilized powder injection, which is directly related to the safety of injection administration. The visible particles and insoluble particles are closely related to the reconstitution property of lyophilized powder injection. After formulation screening, in conjunction with reconstitution property, moisture control and other indexes, it is surprisingly found that the addition of meglumine, tromethamine, arginine and other components is beneficial to the improvement of the reconstitution quality of the lyophilized powder injection after being stored for a period of time and stably guarantee the inspection indicators of visible particles and insoluble particles to be qualified. Preferably meglumine or arginine is added. In the present application, we define such components as stabilizers, which are used for preventing drug precipitation during the reconstitution of lyophilized powder injection and can effectively improve the inspection index of visible particles and insoluble particles. In the existing art, organic solvents such as ethanol and propylene glycol are mostly used as the cosolvent to help dissolve the drug component ketorolac, which can solve the clarity problem of injection to a certain extent and relieve the white spots after sterilization. However, the use of organic alcohols inevitably brings great irritation during administration, which is not beneficial to the popularization and application of drugs.

In a preferred embodiment of the present application, the lyophilized powder injection further includes a stabilizer, where the stabilizer is selected from one or more of meglumine, arginine, lysine or tromethamine, preferably meglumine or arginine, and a mass percentage of the stabilizer in the lyophilized stock solution is 0.1% to 5%, preferably 0.5% to 1%.

Under light and/or high temperature, ketorolac is easy to be decarboxylated and oxidized and then generates 1-keto ketorolac and 1-hydroxy ketorolac, through a process of free radical intermediates in the oxidation state. The addition of antioxidants such as sodium bisulfite can reduce or prevent the generation of free radicals in the oxidation state, so as to reduce the generation of decarboxylation and oxidation impurities. In addition, the oxidation reaction is a complex kind of degradation in stability. The oxidation reaction generally includes the autoxidation of free radicals. Oxidative degradation reaction is greatly affected by light, metal ions (such as copper ions and iron ions), temperature and humidity, solution state or solid state. For example, some drug APIs are insensitive in the solid state but very sensitive in the solution states. Therefore, the addition of an appropriate amount of metal ion chelating agent such as disodium edetate can weaken the catalytic acceleration of metal ions on oxidation and then inhibit the generation of impurities to a certain extent.

In a preferred embodiment of the present application, the lyophilized powder injection further includes one or two of a metal ion chelating agent or an antioxidant, where the metal ion chelating agent is selected from one or more of disodium edetate, sodium calcium edetate, sodium citrate or citric acid, preferably disodium edetate or sodium calcium edetate, and a weight percentage of the metal ion chelating agent in the lyophilized stock solution is 0.05% to 1%; and the antioxidant is selected from one or more of sodium thiosulfate, sodium sulfite, sodium metabisulfite, sodium bisulfite, vitamin C, sodium citrate, citric acid or L-cysteine, preferably sodium bisulfate or vitamin C, and a weight percentage of the antioxidant in the lyophilized stock solution is 0.02% to 2%

In the present application, anhydrous or crystalline water disodium hydrogen phosphate, sodium dihydrogen phosphate, dipotassium hydrogen phosphate or potassium dihydrogen phosphate is preferred as the pH-adjusting agent to maintain the balance between the dissolution of the main drug and the maintenance of the optical stability.

Since phosphate buffer salts are usually divided into the anhydrous substance and hydrates with different crystalline water numbers, it is specified that the disodium hydrogen phosphate mentioned in the summary and embodiments of the present application may be anhydrous disodium hydrogen phosphate, disodium hydrogen phosphate dodecahydrate, disodium hydrogen phosphat monohydrate, disodium hydrogen phosphate dihydrate, disodium hydrogen phosphate pentahydrate or disodium hydrogen phosphate heptahydrate. Unless otherwise specified, disodium hydrogen phosphate dodecahydrate is usually adopted. Similarly, sodium dihydrogen phosphate may be anhydrous sodium dihydrogen phosphate, sodium dihydrogen phosphate monohydrate or sodium dihydrogen phosphate dihydrate. For the application of the above reagents, it should be understood that the same buffering and pH adjustment effects can be achieved by using the same moles, that is, the same amount of substance, anhydrous substances or hydrates with different crystalline water numbers. Because the molecular weights of anhydrous substances or hydrates with different crystalline water numbers are different, the slight difference only reflects in the feed weights. In addition, the situation of dipotassium hydrogen phosphate and potassium dihydrogen phosphate is similar to sodium dihydrogen phosphate, for which, reference is made to the description of sodium dihydrogen phosphate. If there is a similar situation with other reagents, reference is made to the above description, and the details are not repeated here.

In a preferred embodiment of the present application, in the lyophilized powder injection, the active pharmaceutical ingredient is (S)-ketorolac; in the pH-adjusting agent, the buffer is anhydrous or crystalline water disodium hydrogen phosphate; the certain-volume pH-adjusting agent is anhydrous or crystalline water disodium hydrogen phosphate, or an aqueous solution prepared from the same; the lyophilized powder injection further includes a stabilizer meglumine, and the mass percentage of the stabilizer in the lyophilized stock solution is 0.1% to 5%, preferably 0.5% to 1%; and the lyophilized powder injection has optical purity of an active ingredient greater than or equal to 95% in the long-term stability test, that is, after being stored under conditions of 25° C. ±2° C./60% RH ±5% RH for 6 months, and optical purity of an active ingredient greater than or equal to 90% in the accelerated stability test, that is, after being stored under conditions of 40° C. ±2° C./75% RH ±5% RH for 6 months, and more preferably, the lyophilized powder injection has optical purity of an active ingredient greater than or equal to 98% in the long-term stability test, that is, after being stored under conditions of 25° C. ±2° C./60% RH ±5% RH for 6 months, and optical purity of an active ingredient greater than or equal to 95% in the accelerated stability test, that is, after being stored under conditions of 40° C. ±2° C./75% RH ±5% RH for 6 months.

In a preferred embodiment of the present application, in the lyophilized powder injection, the active pharmaceutical ingredient is (S)-ketorolac; in the pH-adjusting agent, the buffer is sodium phosphate or a sodium dihydrogen phosphate hydrate; the certain-volume pH-adjusting agent is sodium hydroxide, phosphoric acid, or an aqueous solution prepared from the same; the lyophilized powder injection further includes a stabilizer arginine, and the mass percentage of the stabilizer in the lyophilized stock solution is 0.1% to 5%, preferably 0.5% to 1%; and the lyophilized powder injection has optical purity of an active ingredient greater than or equal to 95% in the long-term stability test, that is, after being stored under conditions of 25° C. ±2° C./60% RH ±5% RH for 6 months, and optical purity of an active ingredient greater than or equal to 90% in the accelerated stability test, that is, after being stored under conditions of 40° C. ±2° C./75% RH ±5% RH for 6 months, and more preferably, the lyophilized powder injection has optical purity of an active ingredient greater than or equal to 98% in the long-term stability test, that is, after being stored under conditions of 25° C. ±2° C./60% RH ±5% RH for 6 months, and optical purity of an active ingredient greater than or equal to 95% in the accelerated stability test, that is, after being stored under conditions of 40° C. ±2° C./75% RH ±5% RH for 6 months.

In a preferred embodiment of the present application, in the lyophilized powder injection, the active pharmaceutical ingredient is (S)-ketorolac tromethamine salt; in the pH-adjusting agent, the buffer is anhydrous or crystalline water dipotassium hydrogen phosphate or anhydrous or crystalline water potassium dihydrogen phosphate; the certain-volume pH-adjusting agent is a sodium bicarbonate, hydrochloric acid, or an aqueous solution prepared from the same; the lyophilized powder injection further includes a stabilizer arginine, and the mass percentage of the stabilizer in the lyophilized stock solution is 0.1% to 5%, preferably 0.5% to 1%; and the lyophilized powder injection has optical purity of an active ingredient greater than or equal to 95% in the long-term stability test, that is, after being stored under conditions of 25° C. ±2° C./60% RH ±5% RH for 6 months, and optical purity of an active ingredient greater than or equal to 90% in the accelerated stability test, that is, after being stored under conditions of 40° C. ±2° C./75% RH ±5% RH for 6 months, and more preferably, the lyophilized powder injection has optical purity of an active ingredient greater than or equal to 98% in the long-term stability test, that is, after being stored under conditions of 25° C. ±2° C./60% RH ±5% RH for 6 months, and optical purity of an active ingredient greater than or equal to 95% in the accelerated stability test, that is, after being stored under conditions of 40° C. ±2° C./75% RH ±5% RH for 6 months.

In a preferred embodiment of the present application, the lyophilized powder injection further includes a metal ion chelating agent, where the metal ion chelating agent is selected from disodium edetate or sodium calcium edetate, and the weight percentage of the metal ion chelating agent in the lyophilized stock solution is 0.05% to 1%.

In a preferred embodiment of the present application, the lyophilized powder injection further includes an antioxidant, where the antioxidant is selected from sodium bisulfite or vitamin C, and the weight percentage of the antioxidant in the lyophilized stock solution is 0.02% to 2%.

As a preferred embodiment of the present application, feed weight percentages of components in the lyophilized stock solution when the lyophilized powder injection is prepared are as follows:

(S)-ketorolac: 0.5% to 0.7%;
disodium hydrogen phosphate dodecahydrate: 1.8% to 2.0%;
mannitol: 6% to 9%;
disodium edetate: 0.05% to 0.1%;
disodium hydrogen phosphate aqueous solution: appropriate amount, adjusting a pH value to be 6.8 to 7.2; and
water for injection: added to 100%.

The lyophilized stock solution is aseptically filtered, packed and lyophilized to obtain the lyophilized powder injection.

As a preferred embodiment of the present application, feed weight percentages of components in the lyophilized stock solution when the lyophilized powder injection is prepared are as follows:

(S)-ketorolac: 0.5% to 1%;
disodium hydrogen phosphate dodecahydrate: 1.8% to 2.5%;
mannitol: 5% to 15%;
meglumine: 1% to 2%;
disodium hydrogen phosphate aqueous solution: appropriate amount, adjusting a pH value to be 6.8 to 7.2; and
water for injection: added to 100%.

The lyophilized stock solution is aseptically filtered, packed and lyophilized to obtain the lyophilized powder injection.

As a preferred embodiment of the present application, feed weight percentages of components in the lyophilized stock solution when the lyophilized powder injection is prepared are as follows:

(S)-ketorolac tromethamine salt: 0.8% to 1.5%;
potassium dihydrogen phosphate: 0.5% to 1.5%;
mannitol: 5% to 10%;
arginine: 1% to 2%;
dipotassium hydrogen phosphate aqueous solution: appropriate amount, adjusting a pH value to be 6.8 to 7.2; and
water for injection: added to 100%.

The lyophilized stock solution is aseptically filtered, packed and lyophilized to obtain the lyophilized powder injection.

In a second aspect, the present application provides a method for preparing lyophilized powder injection of (S)-ketorolac. The method includes the following steps:

1) dissolving all the auxiliary materials except the active pharmaceutical ingredient and the certain-volume pH-adjusting agent with 70% to 80% water for injection at room temperature under stirring condition, where the auxiliary materials refer to one or more of a buffer, an excipient, a stabilizer, a metal ion chelating agent or an antioxidant, so as to obtain a clear solution;
2) adding (S)-ketorolac or a pharmaceutically acceptable salt thereof, and stirring the mixture for complete dissolution;
3) preparing a certain-volume pH-adjusting agent, slowly adding the certain-volume pH-adjusting agent to the solution obtained in step 2 to adjust pH to be 6.5 to 7.5, preferably 6.8 to 7.2, and more preferably 6.9 to 7.0;
4) supplementing the solution to the constant volume total amount with water for injection, performing aseptic filtration on the drug liquid sequentially through the polyethersulfone filter elements with pore diameters of 0.45 μm, 0.22 μm and 0.22 μm, and performing quality control on the content of the intermediate solution; and
5) packing the drug liquid in a neutral borosilicate glass tube injection bottle, performing the lyophilization procedure by a lyophilization device, and finally, performing corking, removing out of the cabinet and capping, so as to obtain the product of lyophilized powder injection of (S)-ketorolac.

In a third aspect, the present application provides use of lyophilized powder injection of (S)-ketorolac in the preparation of an analgesic drug, and the indication of the analgesic drug specifically is the short-term treatment of acute and severe pain requiring opioid-level analgesics, usually postoperative analgesia. With evaluation and judgment, the lyophilized powder injection of (S)-ketorolac described in the present application can relieve moderate pain and severe postoperative pain, including abdominal pain, chest pain, gynecological pain, oral pain and urological pain, and can also be used to relieve renal colic, biliary colic, toothache, trigeminal neuralgia and cancer pain.

The present application reports for the first time the lyophilized powder injection of (S)-ketorolac or a pharmaceutically acceptable salt thereof (including (S)-ketorolac tromethamine salt and (S)-ketorolac sodium salt) and a preparation method therefor. The lyophilized powder injection has an important use in the preparation of an analgesic drug, and the indication of the analgesic drug is the short-term treatment of acute and severe pain requiring opioid-level analgesics, usually postoperative analgesia.

Compared with the existing art, the present application has the following advantages.

(1) The analgesic activity of ketorolac is resulted from (S)-ketorolac, and its enantiomer (R)-ketorolac has few analgesic effect. Ketorolac tromethamine sold in Chinese and foreign markets is a racemate, which has the defects of frequent administration, gastrointestinal adverse effects common to non-steroidal drugs, poor patient compliance, and the like, and the daily dose is 60 mg to 120 mg, which needs to be administered many times to maintain the efficacy. It is found that (S)-ketorolac can be directly prepared into lyophilized powder injection, or the active pharmaceutical ingredient can be prepared into tromethamine salt, arginine salt, sodium salt and other salt forms of (S)-ketorolac before forming lyophilized preparation, which can reduce the conventional dosage to about 50%, and has the advantages of stable properties, efficiently onset and high safety.

(2) The present application further studies active ingredient (S)-ketorolac or a pharmaceutically acceptable salt thereof (including (S)-ketorolac tromethamine salt, (S)-ketorolac sodium salt, etc.), and it is found that it has intensified degradation and racemization in the aqueous solution and the content of (R)-ketorolac increases with time, so it is necessary to strictly control external conditions to ensure that isomer impurities do not exceed the limit. It is found that the direct preparation of (S)-ketorolac into lyophilized powder injection is beneficial to the maintenance of the optical purity of (S)-ketorolac itself. The content of isomer impurities (R)-ketorolac is controlled within the quality limit by adjusting the formulation and process of the preparation. The technical problems and bottlenecks in maintaining the optical stability of (S)-ketorolac injection are solved by using the optimized formulation and process of lyophilized powder injection.

(3) In the screening process of pH-adjusting agents, it is surprisingly found that although (S)-ketorolac has poor water solubility, it can be dissolved to obtain a clear solution after stirring for a short time under the condition of coexistence with an appropriate proportion of phosphate buffer salt, and the pH value at this time is 6.6 to 6.9, which is lower than neutral 7.0. The phosphate is preferably anhydrous or crystalline water phosphate, including but not limited to disodium hydrogen phosphate, sodium dihydrogen phosphate, dipotassium hydrogen phosphate, potassium dihydrogen phosphate, and sodium phosphate. The above solution can not only improve the solubility and dissolution rate of (S)-ketorolac in water, but also ensure the optical stability in the dissolution process, the preparation of lyophilized powder injection and the storage of the product, which plays an active role in avoiding the excessive increase of isomer impurity (R)-ketorolac and slowing down the racemization rate. Meanwhile, the technical solution reported for the first time avoids using organic solvents such as ethanol and propylene glycol as cosolvents, and avoids using inclusion compounds such as cyclodextrin or non-ionic surfactants such as poloxamer 188, thereby reducing the irritation on blood vessels and muscles during the application of injection and reducing the safety risks such as hemolysis. In a preferred embodiment of the present application, the optical purity of the active ingredient is greater than or equal to 98% in the long-term stability test, that is, after storage under conditions of 25° C. ±2° C./60% RH ±5% RH for 6 months, and the optical purity of the active ingredient is greater than or equal to 95% in the accelerated stability test, that is, after storage under conditions of 40° C. ±2° C./75% RH ±5% RH for 6 months.

(4) The influence of the pH value of the solution on the stability of the main drug is also explored. Acidic conditions are not beneficial to the dissolution of (S)-ketorolac, and the appearance, uniformity and reconstitution performance of the product are all poor. Alkaline condition (pH >7.5) intensifies the degradation and racemization of (S)-ketorolac and makes the content of (R)-ketorolac increase greatly. Therefore, the final suitable pH is determined to be between 6.0 and 7.5, more preferably between 6.8 and 7.2. The physicochemical stability of (S)-ketorolac or a pharmaceutically acceptable salt thereof (including (S)-ketorolac tromethamine salt, (S)-ketorolac sodium salt and (S)-ketorolac arginine salt) is the best under this pH condition.

(5) The lyophilization process and product moisture control are studied deeply. Two stages, pre-freezing and sublimation drying, are paid attention to, and the temperature and time parameters of each stage are reasonably set to ensure the quality of lyophilized products. The moisture content of the lyophilized product prepared by the method is controlled at less than or equal to 2%. In the existing art, the moisture content of lyophilized powder injection is generally higher than 2%, usually 3% to 5%. As is well-known, ketorolac itself is prone to degradation under high temperature, light and acid-base conditions, color deepening, and decarboxylation and oxidation to produce impurities, which affects the safety of clinical medication to a certain extent, and the degradation rate of ketorolac in the solution state is obviously faster than that in the solid state. Leaving the chemical instability caused by ketorolac, the optical stability of (S)-ketorolac also needs to be attached attention on, whose chiral atoms are extremely easy to be racemized. Therefore, the moisture content of (S)-ketorolac lyophilized preparation is controlled within a reasonable range, which is beneficial to the improvement of the chemical stability and optical stability of samples during storage.

(6) When (S)-ketorolac or a pharmaceutically acceptable salt thereof (including (S)-ketorolac tromethamine salt, (S)-ketorolac sodium salt and (S)-ketorolac arginine salt) described in the present application is used as the active pharmaceutical ingredient, the process is stable, and the operation is convenient, which satisfies the requirements of industrial mass production.

(7) In a preferred embodiment of the present application, a stabilizer such as arginine or meglumine is added, which can effectively improve the clarity detection results of visible particles and insoluble particles in the reconstitution solution of the lyophilized powder injection which is stored for a period of time.

(8) In a preferred embodiment of the present application, a metal ion chelating agent or an antioxidant is added, which is beneficial to the reduction of decarboxylation and oxidation impurities generated during preparation and sample storage of pharmaceutical components, such as 1-keto ketorolac, 1-hydroxy ketorolac and other impurities and can also inhibit the stereo conversion of (S)-ketorolac to a certain extent.

DETAILED DESCRIPTION

To make the above aspects, features and advantages of the present disclosure clearer, the detailed description of the present disclosure is described in detail in conjunction with accompanying drawings and specific examples. Details are set forth below to facilitate a thorough understanding of the present disclosure. However, the present disclosure may be implemented by other manners different from those described herein, and those skilled in the art may make similar extensions without departing from the spirit of the present disclosure. Therefore, the present disclosure is not limited to the specific examples described below.

Test Example 1 Preparation and Structure Confirmation of (S)-ketorolac

The preparation of (S)-ketorolac has been reported in the existing literature. Fulling et al. (J. Am. Chem. Soc., 1987, 109, 2845) reported a method in which S-ketorolac was obtained by enzymatic selective catalytic hydrolysis of ketorolac ester, and the product had high optical purity. Guzman et al. (J. Med. Chem., 1986, 29, 589-591) used L-cinchonidine to react with ketorolac to form a salt and separated ketorolac by crystallization. Angel et al. (Tetrahydron: Asymmetry, 1992, 3(11), 1455) made ketorolac react with an optically active alcohol to form an ester, separated the ester by high performance liquid chromatography (HPLC) and then hydrolyzed the ester to obtain (+)- or (−)-ketorolac.

In the present application, (S)-ketorolac samples were obtained by using the method of separation with cinchonidine. The preparation process is described below.

11.7 g of L-cinchonidine was dissolved in 200 mL of hot absolute ethanol and added to a solution of 10.2 g of racemic ketorolac in 50 mL of ethyl acetate. The resulting mixture was heated to reflux and then reacted for 0.5 hour, the solvent was removed under reduced pressure, and the residue was recrystallized with 200 mL of ethyl acetate to give about 3.7 g of (S)-ketorolac.

1) The specific rotation ranged from −176° to −177° (c=0.1, ethanol).

Figure 1:
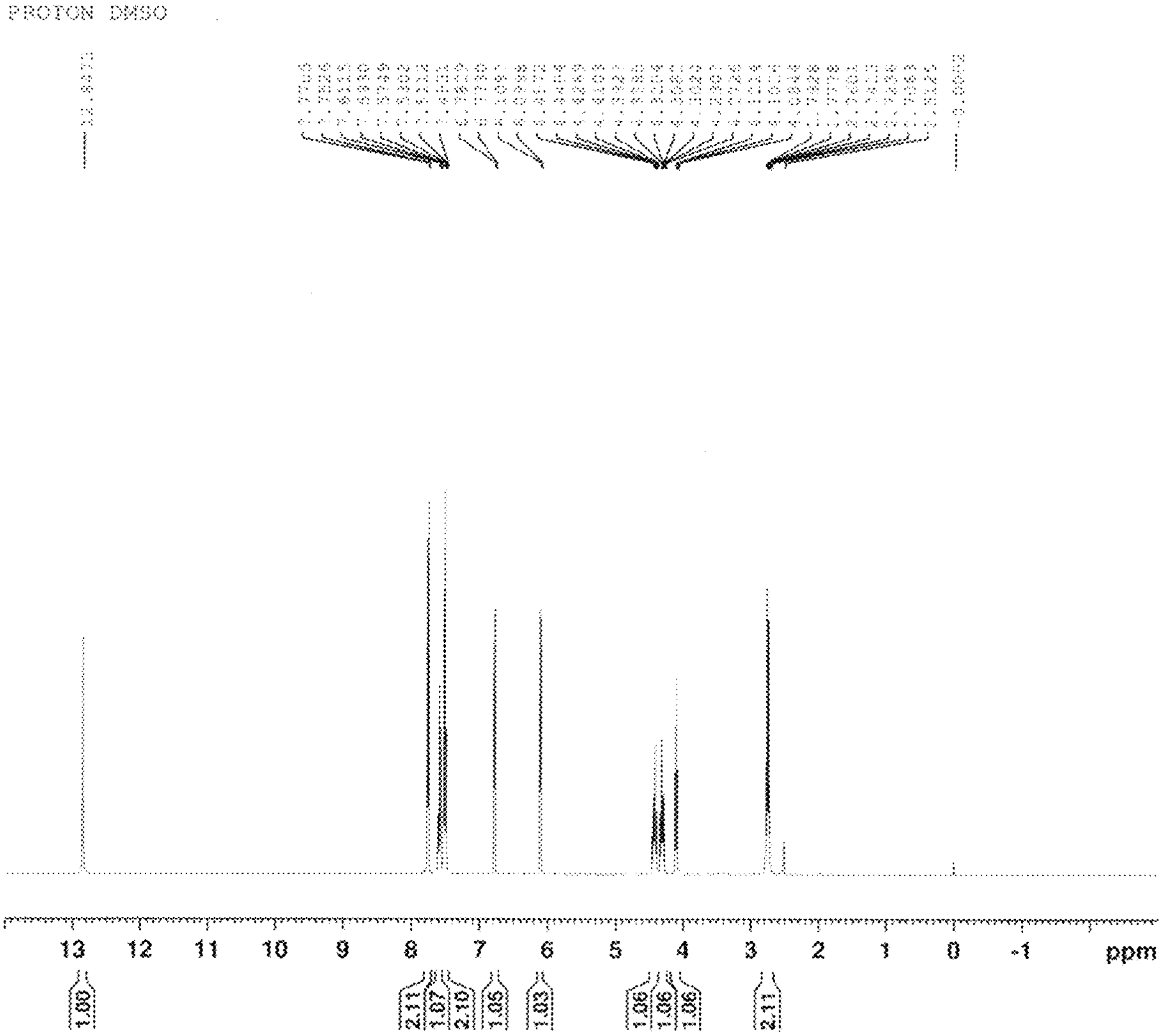
FIG. 1 is the $^{1}H$ NMR spectrum of (S)-ketorolac.

2) The $^{1}H$ NMR spectrum data are as follows, and see FIG. 1.

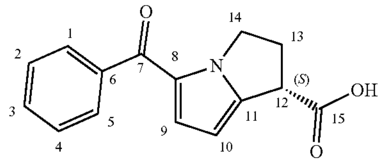

| Proton No. | Chemical shift (ppm) | Multi-plicity | Proton number | 1H-1H COSY | NOESY | Notes |
|---|---|---|---|---|---|---|
| 15-COOH | 12.8473 | s | 1 | / | / | / |
| 1, 5 | 7.7705 | d | 2 | 7.6115<br>7.5302 | 7.5302<br>6.7829 | J = 7.2 Hz |
| 3 | 7.6115 | t | 1 | 7.7705<br>7.5302 | / | / |
| 2, 4 | 7.5302 | d | 2 | 7.7705<br>7.6115 | 7.7705 | J = 14.8 Hz |
| 9 | 6.7829 | d | 1 | 6.1097 | 7.7705 | J = 4.0 Hz |
| 10 | 6.1097 | d | 1 | 6.7829 | / | J = 4.0 Hz |
| 14a | 4.4572-4.3927 | m | 1 | 4.3385-4.2907<br>2.7928 | / | / |
| 14b | 4.3385-4.2907 | m | 1 | 4.4572-4.3927<br>2.7928 | / | / |
| 12 | 4.2726 | t | 1 | 2.7928 | / | / |
| 13 | 2.7928 | m | 2 | 4.4572-4.3927<br>4.3385-4.2907<br>4.2726 | / | / |

Figure 2:
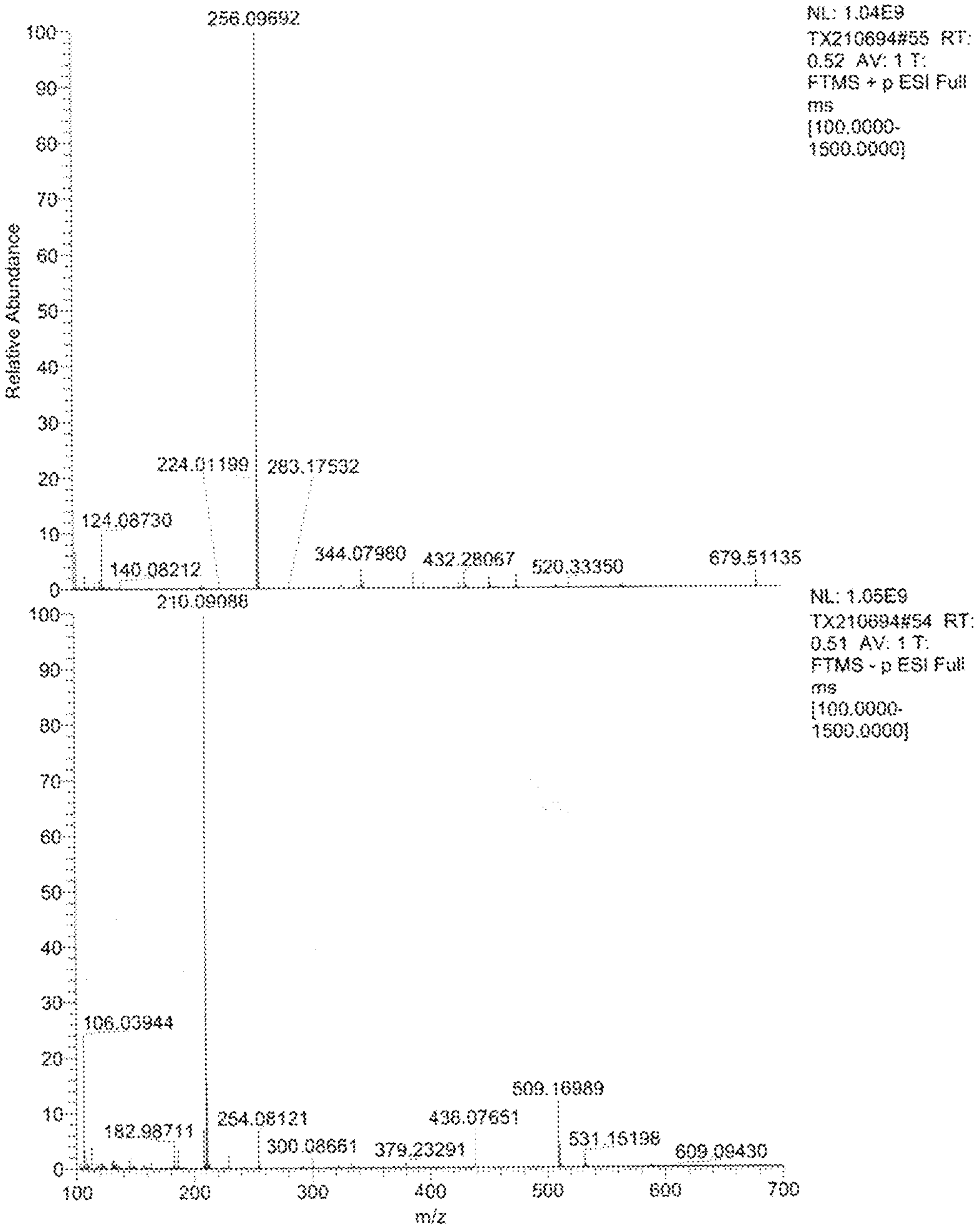
FIG. 2 is the high resolution mass spectrum of (S)-ketorolac.
Figure 3:
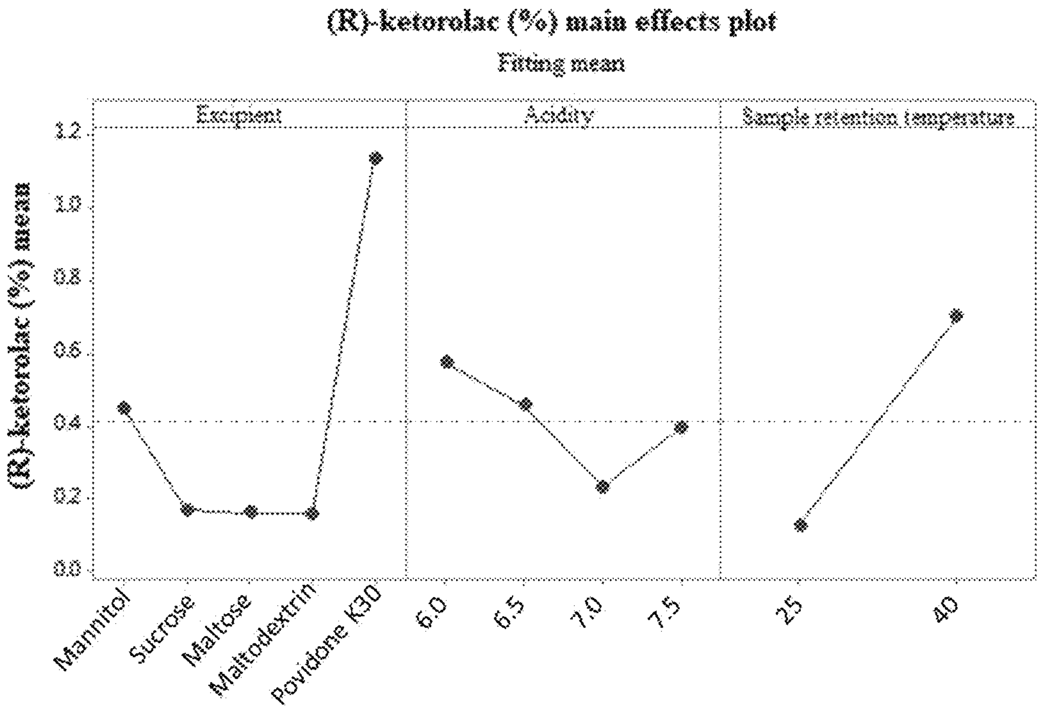
FIG. 3 is the main effects plot of the formulation on the isomer impurity (R)-ketorolac (%).
Figure 4:
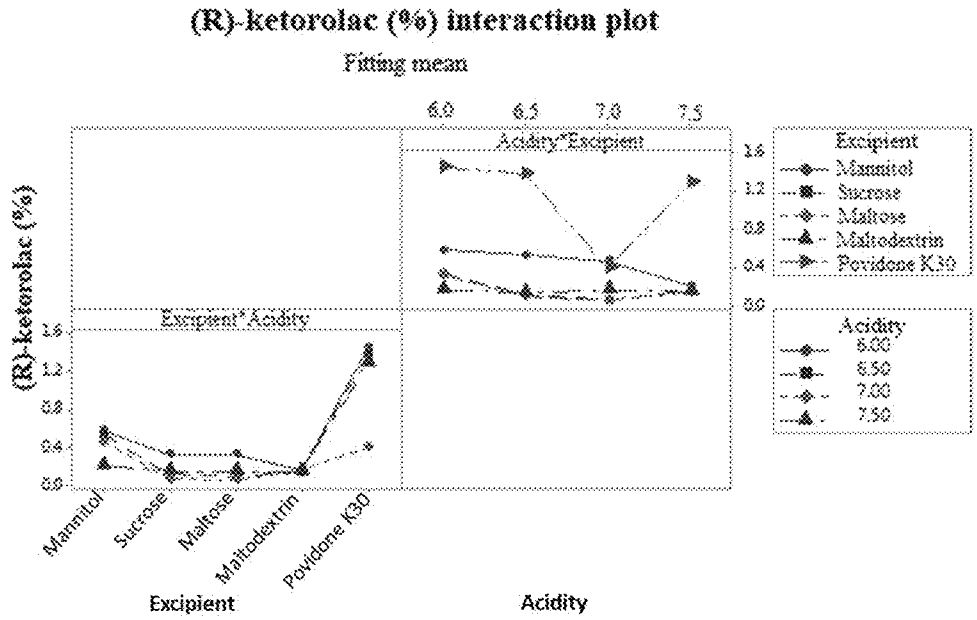
FIG. 4 is the interaction plot of the formulation on the isomer impurity (R)-ketorolac (%).
Figure 5:
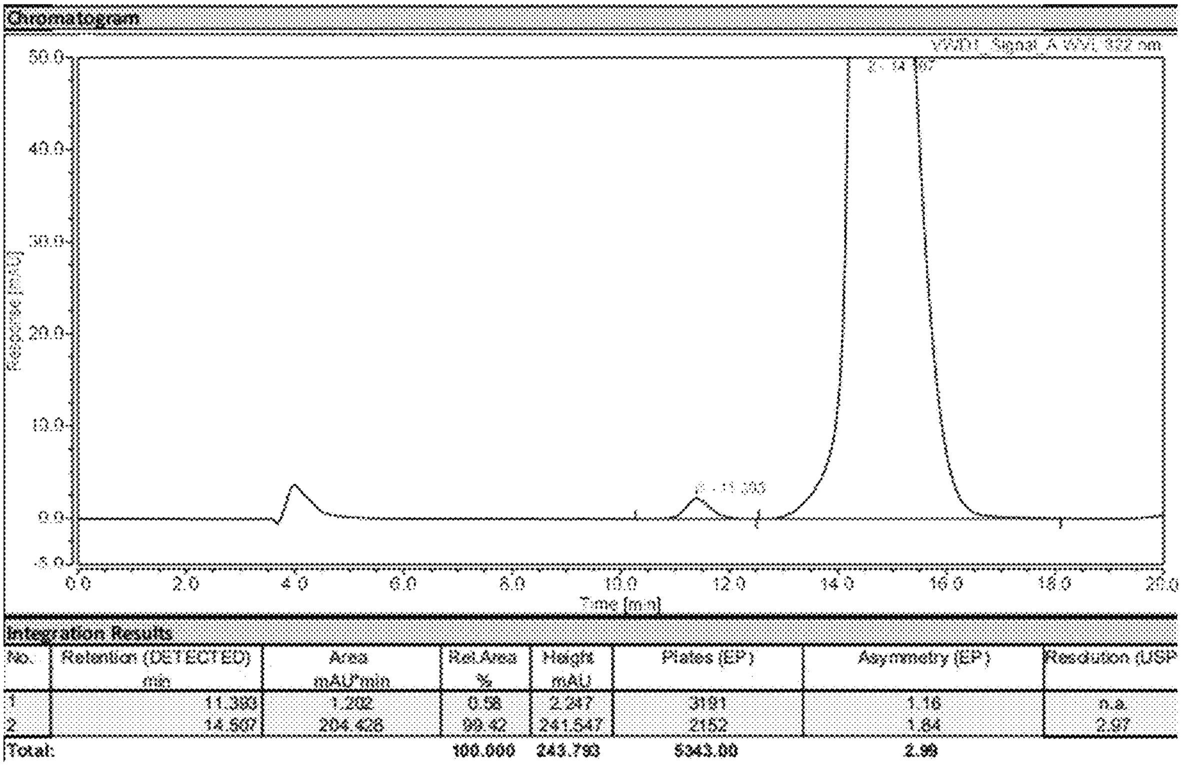
FIG. 5 is a representative graph of the stability test of the lyophilized powder injection described in the present application stored at 25° C. for 6 months.
Figure 6:
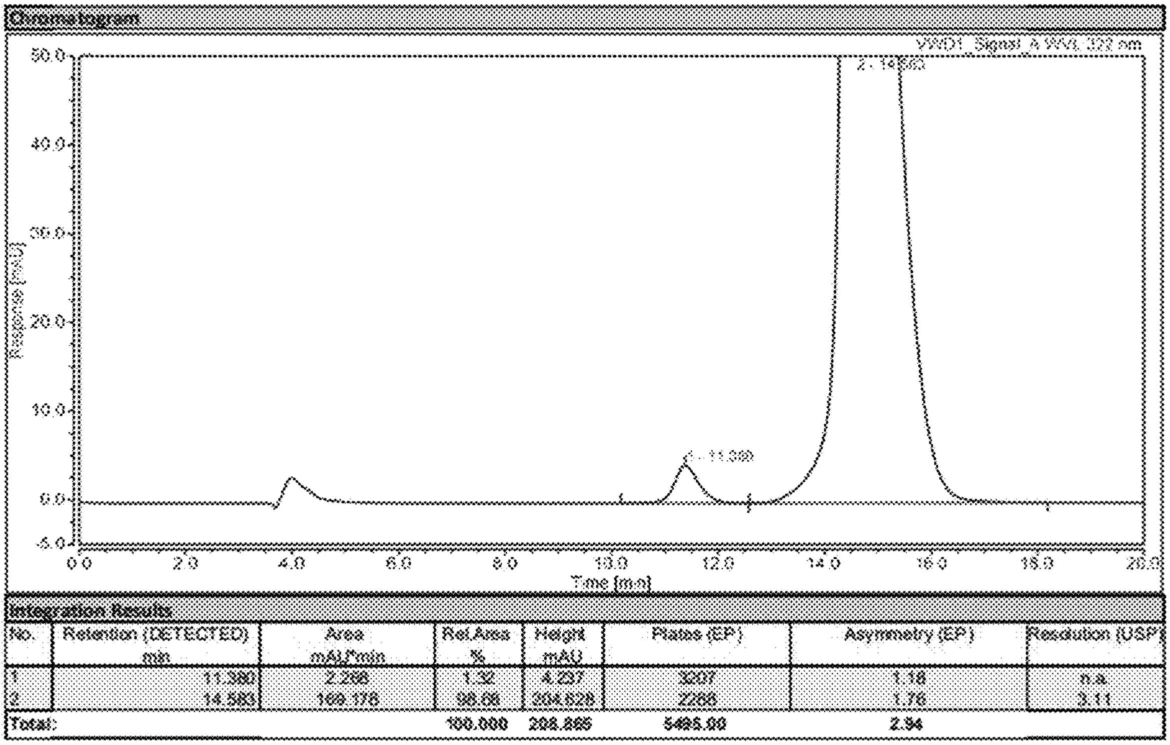
FIG. 6 is a representative graph of the stability test of the lyophilized powder injection described in the present application stored at 40° C. for 6 months.

3) The high resolution mass spectrum data are as follows, and see FIG. 2.

| Mass-to-charge ratio (m/z) | Intensity | Assignment | Notes |
|---|---|---|---|
| 256.09692 | 100% | $([C_{15}H_{13}NO_3] + H)^+$ | ESI |

In the positive ion mode, the m/z of $([C_{15}H_{13}NO_3]+H)^+$ was 256.09692, indicating that the mass-to-charge ratio of the tested sample was 255.089808, and the calculated molecular composition was $C_{15}H_{13}NO_3$, which conformed to the target molecular structure.

Because of the poor water solubility of (S)-ketorolac, the aqueous solution was prone to degradation and color changing under high temperature or light, which made the related substances and the isomer impurity (R)-ketorolac increase. Therefore, (S)-ketorolac prepared into common salt forms was investigated, such as (S)-ketorolac sodium salt and (S)-ketorolac arginine salt. The method for preparing conventional salt forms is generally described as follows:

(S)-ketorolac and equimolar base were dissolved in absolute ethanol and stirred for 0.5 hour to 2 hours at room temperature, then the solvent was removed under reduced pressure, ethyl acetate and/or n-hexane were added, and the obtained solid precipitate was subjected to suction filtration, and drying under reduced pressure to give a salt form product.

Test Example 2 Solubility test of (S)-ketorolac in Phosphate Buffer Solutions with Different pH After (S)-ketorolac was further prepared into (S)-ketorolac tromethamine salt and (S)-ketorolac sodium salt, the stability of the active pharmaceutical ingredient in the solid state was improved, the stability at high temperature, high humidity and strong light irradiation was significantly improved, and the appearance was always white or off-white without color deepening. However, in the aqueous solution, the degradation and racemization of (S)-ketorolac were intensified at high temperature, that is, the content of (R)-ketorolac was prone to increasing significantly.

The solubility of (S)-ketorolac in the aqueous solution was poor. In the process of screening pH-adjusting agents, it was surprisingly found that the addition of phosphate, that is, disodium hydrogen phosphate or/and sodium dihydrogen phosphate, to the aqueous solution of (S)-ketorolac could not only improve the solubility of the main drug ketorolac in water, but also greatly improve the optical stability of (S)-ketorolac in the preparation and slow down the racemization rate under the accelerated stability test conditions.

Phosphate buffer solutions with a pH range of 6.5 to 7.8 were prepared with reference to Chinese Pharmacopoeia (2020 edition). The appropriate amount of (S)-ketorolac (free acid) was added to each phosphate buffer to prepare mixtures of about 20 mg/ml. Each solution was placed in an air bath shaker and shaken at 25° C. for 24 hours, during which the dissolution of (S)-ketorolac in each mixture was observed. The solubility of the compound at 25° C. after one day was detected under various pH conditions, as shown in Table 1. The remaining samples were reserved at 25° C. and 40° C., and the formation of isomers was detected after 2 days and 30 days, as shown in Table 2.

TABLE 1

| Solubility of (S)-ketorolac in phosphate buffer solutions with different pH values | |
|---|---|
| Phosphate buffer solution pH | Saturation solubility at 25° C. (mg/mL) |
| 6.5 | 1.862 |
| 6.8 | 3.027 |
| 7.0 | 4.094 |
| 7.2 | 4.519 |
| 7.4 | 4.716 |
| 7.6 | 5.219 |
| 7.8 | ≥24.232 |

TABLE 2

| Optical stability of (S)-ketorolac in phosphate buffer solutions with different pH values | | | |
|---|---|---|---|
| | Isomer purity determined (%) | | |
| pH | 25° C., Day 2 | 25° C., Day 30 | 40° C., Day 30 |
| 6.5 | 0.20 | 3.43 | 27.90 |
| 6.8 | 0.21 | 3.22 | 28.14 |
| 7.0 | 0.22 | 3.20 | 27.11 |
| 7.2 | 0.22 | 3.34 | 27.71 |
| 7.4 | 0.21 | 3.31 | 23.91 |
| 7.6 | 0.22 | 3.43 | 24.35 |
| 7.8 | 0.51 | 4.92 | 21.28 |

The results show that: 1) (S)-ketorolac had pH-dependent dissolution, its solubility increased with the increase of acidity, and the solubility of (S)-ketorolac jumped in the phosphate buffer solution with pH of 7.8; 2) for samples in the solution state, the optical purity of (S)-ketorolac was greater than or equal to 95% when samples were stored at 25° C. for one month, but the generated isomer (R)-ketorolac increased significantly when samples were stored at 40° C. for one month, indicating that the degradation and racemization of (S)-ketorolac in phosphate buffer solution were still intensified at high temperature, and the optical stability of (S)-ketorolac needed to be improved by technical means.

To sum up, (S)-ketorolac or the pharmaceutically acceptable salts thereof (including (S)-ketorolac tromethamine salt and (S)-ketorolac sodium salt) was probably not suitable for being prepared into conventional injection of aqueous solution to maintain its optical purity, and it was necessary to further study and develop suitable dosage forms to solve the above technical problems. Compared with injection of aqueous solution, lyophilized powder injection was expected to maintain the optical purity of drugs, because (S)-ketorolac was not prone to oxidization when being prepared in vacuum and its water content was very low so that the degradation probability caused by water catalysis was low. In addition, the special production process of lyophilized powder injection made the drugs evenly dispersed in the lyophilized protective agent, which provided a stable preparation environment. In conclusion, (S)-ketorolac or the pharmaceutically acceptable salt thereof (including (S)-ketorolac tromethamine salt and (S)-ketorolac sodium salt) was suitable for being prepared into lyophilized powder injection, so as to solve the problem that it is difficult to maintain the optical purity and physical and chemical stability of the active ingredient (S)-ketorolac in injection aqueous solution.

Test Example 3 Screening and Examination of Excipients in Preparations and pH Value of Lyophilized Stock Solution The preparation method is as follows: an excipient and a pH-adjusting agent sodium dihydrogen phosphate dodecahydrate were dissolved with 70% to 80% water for injection to obtain a clear solution, (S)-ketorolac was added to the clear solution and stirred to be dissolved, and pH was adjusted with disodium hydrogen phosphate solution; the solution was supplemented to the constant volume total amount with water for injection; after aseptic filtration and lyophilization procedure, the product of lyophilized powder injection of (S)-ketorolac was obtained.

The product was stored under the conditions of 25° C. and 40° C. for 20 days, and the content change of (R)-ketorolac in lyophilized powder injection was examined under the conditions of different excipients and different pH values of lyophilized stock solution. The results are shown in Table 4.

TABLE 3

| Effects of different excipients and different pH values of lyophilized stock solution | | | |
|---|---|---|---|
| Examination condition | | | |
| | pH of lyophilized | Detection on Day 20 | |
| Excipient type | stock solution | 25° C. | 40° C. |
| Mannitol | 6.0 | 0.08 | 1.08 |
| | 6.5 | 0.18 | 0.89 |
| | 7.0 | 0.15 | 0.77 |
| | 7.5 | 0.12 | 0.30 |
| Sucrose | 6.0 | 0.05 | 0.61 |
| | 6.5 | 0.05 | 0.19 |
| | 7.0 | 0.04 | 0.09 |
| | 7.5 | 0.06 | 0.24 |
| Maltose | 6.0 | 0.06 | 0.60 |
| | 6.5 | 0.05 | 0.14 |
| | 7.0 | 0.05 | 0.07 |
| | 7.5 | 0.06 | 0.24 |
| Maltodextrin | 6.0 | 0.07 | 0.26 |
| | 6.5 | 0.08 | 0.20 |
| | 7.0 | 0.08 | 0.25 |
| | 7.5 | 0.08 | 0.22 |
| Povidone K30 | 6.0 | 0.40 | 2.50 |
| | 6.5 | 0.41 | 2.35 |
| | 7.0 | 0.12 | 0.68 |
| | 7.5 | 0.29 | 2.30 |

TABLE 4

| Properties of products obtained with different excipients | | |
|---|---|---|
| Excipient for lyophilizing | Sample retention condition | Lyophilized product property |
| Mannitol | Day 0 | White loose solid |
| | 25° C., Day 20 | White loose solid |
| | 40° C., Day 20 | White loose solid |
| Sucrose | Day 0 | White loose and porous solid |
| | 25° C., Day 20 | Off-white, loose, flaky and multilayered solid |
| | 40° C., Day 20 | yellowish shrinking columnar lump surrounded by flaky solid |
| Maltose | Day 0 | White loose solid with uneven surfaces |
| | 25° C., Day 20 | White, with an uneven upper surface and loose and raised bottom |
| | 40° C., Day 20 | Yellow, with loose and raised bottom and porous surfaces |

TABLE 4-continued

| Properties of products obtained with different excipients | | |
|---|---|---|
| Excipient for lyophilizing | Sample retention condition | Lyophilized product property |
| Maltodextrin | Day 0 | White loose solid |
| | 25° C., Day 20 | White loose solid |
| | 40° C., Day 20 | White loose solid |
| Povidone K30 | Day 0 | White loose solid |
| | 25° C., Day 20 | White loose solid |
| | 40° C., Day 20 | White loose solid |

The results show that for the appearance properties of lyophilized preparations after being reserved at different temperatures, the lyophilized samples with mannitol, maltodextrin and povidone K30 as excipients satisfied the requirements. According to the analysis of isomer detection results under different sample retention conditions, the lyophilized samples with sucrose, maltose, maltodextrin and mannitol as excipients satisfied the requirements. In conclusion, the preferred excipients were maltodextrin and mannitol.

Test Example 4 Examination of Optical Stability of Lyophilized Powder Injection Diluted with Normal Saline

TABLE 5

Examination of (R)-ketorolac diluted with normal saline

| Reconstitution solution name | pH after reconstitution | Sample retention temperature (° C.) | (R)-ketorolac (%) Sample retention for 24 hours | Sample retention for 7 days |
|---|---|---|---|---|
| 0.17 mg/mL pH 7.2 mannitol lyophilized preparation normal saline solution of (S)-ketorolac | 7.17 | 25 | 0.43 | 0.39 |
| | | 40 | 0.48 | 0.62 |
| 0.17 mg/mL pH 7.0 mannitol lyophilized preparation normal saline solution of (S)-ketorolac | 7.01 | 25 | 0.34 | 0.48 |
| | | 40 | 0.39 | 0.73 |
| 5 mg/mL pH 7.0 mannitol lyophilized preparation normal saline solution of (S)-ketorolac | 7.02 | 5 | 0.43 | 0.53 |
| | | 25 | 0.46 | 0.58 |
| | | 40 | 0.58 | 1.12 |

The results show that the isomers in each (S)-ketorolac lyophilized preparation did not increase significantly after sample retention at 25° C. for 24 hours, but increased slightly after sample retention at 40° C. for 24 hours, which was still within the controllable mass range.

Test Example 5 Stability Examination of Lyophilized Powder Injection Prepared from (S)-ketorolac Free Acid and Different Salt Forms The preparation method was similar to the preparation method in Test Example 3. The pH-adjusting agent was disodium hydrogen phosphate or/and sodium dihydrogen phosphate, and the addition amount of the pH-adjusting agent varied with the content of the main drug (S)-ketorolac or the pharmaceutically acceptable salt thereof, and the concentration was 3 mg/ml to 7.5 mg/ml, more preferably 5 g/ml. After the samples were stored for 6 months under the conditions of the accelerated test (temperature of 40±2° C. and relative humidity of 75±5° C.), the changes of sample content, (R)-ketorolac content, appearance, property, reconstitution and other indexes were examined. The results are shown below.

TABLE 6

Examination of optical stability of lyophilized powder injection prepared from different active pharmaceutical ingredients

| Formulation | Formulation 1 | Formulation 2 | Formulation 3 | Formulation 4 | Formulation 5 | Formulation 6 |
|---|---|---|---|---|---|---|
| (S)-ketorolac/g | 1.0 | / | / | 1.0 | / | / |
| (S)-ketorolac tromethamine salt/g | / | 1.5 | / | / | 1.5 | / |

TABLE 6-continued

Examination of optical stability of lyophilized powder injection prepared from different active pharmaceutical ingredients

| Formulation | | Formulation 1 | Formulation 2 | Formulation 3 | Formulation 4 | Formulation 5 | Formulation 6 |
|---|---|---|---|---|---|---|---|
| (S)-ketorolac sodium salt/g | | / | / | 1.1 | / | / | 1.1 |
| Mannitol/g | | 10 | 10 | 10 | 10 | 10 | 10 |
| Disodium hydrogen phosphate/g | | / | 1.27 | / | 1.27 | / | 0.64 |
| Sodium dihydrogen phosphate/g | | / | / | 1.27 | / | 1.27 | 0.64 |
| Water for injection added to/mL | | 200 | 200 | 200 | 200 | 200 | 200 |
| Formulation amount/bottle | | 50 | 50 | 50 | 50 | 50 | 50 |
| Appearance | | Light yellow | Off-white to light yellow | Off-white to light yellow | Off-white to light yellow | Off-white to light yellow | Off-white to light yellow |
| Property | | Agglomer | Puffy and ation texture | Puffy and loose texture | Puffy and loose texture | Puffy and loose texture | Puffy and loose texture |
| Reconstitution | | Slow and incomplete | Fast and complete | Fast and complete | Fast and complete | Fast and complete | Fast and complete |
| Day 0 | (S)-ketorolac/% | 96.36 | 98.82 | 96.45 | 99.28 | 96.67 | 95.58 |
| | (R)-ketorolac/% | 3.64 | 1.18 | 3.55 | 0.72 | 3.33 | 4.42 |
| Acceleration for 6 months | (S)-ketorolac/% | 60.81 | 93.63 | 87.36 | 96.92 | 86.17 | 87.86 |
| | (R)-ketorolac/% | 39.19 | 6.37 | 12.64 | 3.08 | 13.83 | 10.14 |

The results show that compared with Formulation 1 without any pH-adjusting agent added, after disodium hydrogen phosphate or/and sodium dihydrogen phosphate were added, Formulations 2 to 6 reduced the racemization of (S)-ketorolac.

Test Example 6 Examination of the Stability of Samples Prepared Under Conditions of Mannitol and Different pH Values The preparation method was similar to the preparation method in Test Example 3. After the samples were stored for 15 days at room temperature (25±2° C.) and under the conditions of the accelerated test (temperature of 40±2° C. and relative humidity of 75±5° C.), the changes of the (R)-ketorolac content, property, reconstitution rate and other indexes of samples were examined. The results are shown in Table 7.

TABLE 7

Examination of the property of samples prepared under different pH conditions

| Sample Name | Sample retention temperature (° C.) | Sample retention time (days) | (R)-ketorolac (%) | Property | Reconstitution rate |
|---|---|---|---|---|---|
| (S)-ketorolac-mannitol pH 6.0 | / | 0 | 0.03 | Yellow to off-white lump | Slow |
| lyophilized preparation | 25 | 14 | 0.16 | Yellow to off-white lump | Slow |
| | | 44 | 0.31 | Yellow to off-white lump | Slow |

TABLE 7-continued

Examination of the property of samples prepared under different pH conditions

| Sample Name | Sample retention temperature (° C.) | Sample retention time (days) | (R)-ketorolac (%) | Property | Reconstitution rate |
|---|---|---|---|---|---|
| | 40 | 14 | 0.30 | Yellow to off-white lump | Slow |
| | | 44 | 0.79 | Yellow to off-white lump | Slow |
| (S)-ketorolac-mannitol pH 6.5 lyophilized preparation | / | 0 | 0.03 | White lump | Moderate |
| | 25 | 14 | 0.12 | White lump | Fast |
| | | 44 | 0.30 | White lump | Fast |
| | 40 | 14 | 0.25 | White lump | Fast |
| | | 44 | 0.89 | White lump | Fast |
| (S)-ketorolac-mannitol pH 7.0 lyophilized preparation | / | 0 | 0.04 | White lump | Fast |
| | 25 | 14 | 0.09 | White lump | Fast |
| | | 44 | 0.14 | White lump | Fast |
| | 40 | 14 | 0.10 | White lump | Fast |
| | | 44 | 0.38 | White lump | Fast |
| (S)-ketorolac-mannitol pH 7.5 lyophilized preparation | / | 0 | 0.04 | White lump | Fast |
| | 25 | 14 | 0.08 | White lump | Moderate |
| | | 44 | 0.15 | White lump | Moderate |
| | 40 | 14 | 0.10 | White lump | Moderate |
| | | 44 | 0.74 | White lump | Moderate |
| (S)-ketorolac-mannitol pH 7.8 lyophilized preparation | / | 0 | 0.07 | Yellow to off-white lump | Slow |
| | 25 | 14 | 0.10 | Yellow to off-white lump | Slow |
| | | 44 | 0.21 | Yellow to off-white lump | Slow |
| | 40 | 14 | 0.18 | Yellow to off-white lump | Slow |
| | | 44 | 0.79 | Yellow to off-white lump | Slow |

The results show that when the pH was in the range of 6.0 to 7.5, acidic conditions were not beneficial to the dissolution of the active ingredient (S)-ketorolac, and both the formability and reconstitution effect of prepared products were poor. With the increase of pH, the rate of (S)-ketorolac performing conformational inversion to form (R)-ketorolac was very low, indicating that the optical stability of (S)-ketorolac lyophilized preparation was better. When the pH value was greater than 7.5, the rate of (S)-ketorolac performing conformational inversion to form (R)-ketorolac increased, the content of (R)-ketorolac in the lyophilized preparation increased, and the optical stability of the reconstituted solution decreased. When pH was 7.8, the reconstitution rate of lyophilized preparation was slow, and the lyophilized preparation could be dissolved by vortex, which was not beneficial to clinical use.

Test Example 7 Exploration of the Lyophilization Process

For freezing control (i.e., pre-freezing) and sublimation drying stages, the changes of appearance, property, reconstitution, water content and other indexes of samples at different temperatures and times in each stage were examined. The results are shown in Table 8.

TABLE 8

Exploration and examination of lyophilization parameters

| Index | 1 | 2 | 3 | 4 | 5 |
|---|---|---|---|---|---|
| Pre-freezing temperature/° C. | −5° C. | −5° C. | −5° C. | −10° C. | −10° C. |
| Pre-freezing time/h | 1 h | 2 h | 2 h | 2 h | 2 h |
| Freezing temperature/° C. | −20° C. | −30° C. | −35° C. | −40° C. | −40° C. |
| Freezing duration/h | 3 h | 5 h | 5 h | 4 h | 5 h |
| Low-temperature sublimation temperature/° C. | −20° C. to 0° C. | −20° C. to 0° C. | −20° C. to 0° C. | −20° C. to 0° C. | −20° C. to 0° C. |
| Low-temperature sublimation time/h | 3 h | 8 h | 8 h | 10 h | 12 h |
| Vacuum drying temperature/° C. | 10° C. to 20° C. | 10° C. to 20° C. | 10° C. to 20° C. | 10° C. to 20° C. | 10° C. to 20° C. |
| Vacuum drying time/h | 4 h | 6 h | 8 h | 10 h | 12 h |

TABLE 8-continued

| Exploration and examination of lyophilization parameters | | | | | |
|---|---|---|---|---|---|
| Index | 1 | 2 | 3 | 4 | 5 |
| Appearance | Off-white to light yellow | Off-white to light yellow | Off-white to light yellow | Off-white to light yellow | Off-white to light yellow |
| Property | Agglomeration | Puffy and loose texture | Puffy and loose texture | Puffy and loose texture | Puffy and loose texture |
| Reconstitution | Slow and incomplete | Fast and complete | Fast and complete | Fast and complete | Fast and complete |
| Water content/% | 5.63 | 1.86 | 1.88 | 1.96 | 2.02 |

The results show that the samples prepared according to lyophilization process 1 had poor properties and high water content, while the samples prepared according to lyophilization processes 2 to 5 had good properties and low water content. Therefore, the optimum lyophilization process was determined as follows: after partially stoppering, the samples were subjected to pre-freezing at −5° C. to −10° C. for 2 hours, cooling to −40° C. and keeping for 3 hours, heating to −20° C. to 0° C., sublimation drying for 8 hours to 12 hours, then heating to 10° C. to 20° C. and vacuum drying for 6 hours to 12 hours, and then complete stoppering and removing out of the cabinet, and the lyophilization process was finished.

Test Example 8 Effect Examination of Stabilizers

| Example/ unit dosage formulation | 1 | 2 | 3 | 4 | 5 | 6 |
|---|---|---|---|---|---|---|
| (S)-ketorolac | 10 mg | 10 mg | 10 mg | 10 mg | 10 mg | 10 mg |
| Meglumine | 0 | 1 mg | 10 mg | 20 mg | 50 mg | 100 mg |
| Disodium hydrogen phosphate/ phosphoric acid | adjusting pH to 6.9 to 7.1 | | | | | |
| Mannitol | 100 mg | 100 mg | 100 mg | 100 mg | 100 mg | 100 mg |
| Water for injection | 2 g | 2 g | 2 g | 2 g | 2 g | 2 g |
| pH value before lyophilizing | 7.00 | 7.01 | 7.00 | 6.98 | 7.00 | 6.99 |

The formulation amount of water for injection was weighted out and stirred at room temperature, the formulation amount of meglumine and mannitol were added, after complete dissolution, the formulation amount of (S)-ketorolac was added, the acidity value of drug liquid was measured, and the solution pH was adjusted to 6.9 to 7.1 with disodium hydrogen phosphate or phosphoric acid. The drug liquid was subjected to aseptic filtration sequentially through the polyethersulfone filter elements with pore diameters of 0.45 μm, 0.22 μm and 0.22 μm, and the content of the intermediate solution was measured. The drug liquid was packed into 5 mL neutral borosilicate glass tube injection bottles, the packing amount was determined according to the content of intermediates, and the specification was that each bottle contained 10 mg of (S)-ketorolac.

The lyophilization procedure is as follows:

a. Pre-freezing: the temperature was lowered to −5° C. within 20 minutes and kept for 1 hour; the temperature was lowered to −10° C. within 20 minutes and kept for 1 hour; the temperature was lowered to −30° C. within 20 minutes and kept for 6 hours; and the pre-freezing was finished.

b. Sublimation drying: the vacuum degree in the freeze dryer was adjusted to less than or equal to 20 pa for vacuum drying; the temperature was raised to −20° C. within 20 minutes and kept for 9 hours; the temperature was raised to −10° C. within 20 minutes and kept for 8 hours; the temperature was raised to 0° C. within 20 minutes and kept for 8 hours; and the sublimation drying was finished.

c. Vacuum drying: the vacuum degree in the freeze-dryer was kept less than or equal to 20 pa, and the temperature was raised to 10° C. within 20 minutes and kept for 6 hours; the vacuum degree in the freeze-dryer was adjusted to less than or equal to 10 pa, and the temperature was raised to 20° C. within 20 minutes and kept for 6 hours; the vacuum degree in the freeze-dryer was kept less than or equal to 10 pa, and the temperature was raised to 30° C. within 20 minutes and kept for 3 hours; and the vacuum drying was finished.

d. Corking and removing out of the cabinet were performed, and the lyophilizing was finished.

I. Examination from the perspective of visible particles and insoluble particles in the reconstituted preparation Several samples of each example were stored in constant temperature and humidity boxes at 5° C., 25° C. and 40° C. respectively. After 6 months, two bottles of samples of each example were taken out under respective sample retention condition. 2 ml of normal saline was added undisturbedly at room temperature for reconstitution, and the time required for the complete dissolution of lumps in the bottle was recorded. For the reconstituted solution, the visible particle light test was performed with reference to Item 0904 General notice of the Chinese Pharmacopoeia (2020 edition), and if there was no visible particles visible to naked eyes, the insoluble particles microscopic observation was performed with reference to Item 0903 General notice of the Chinese Pharmacopoeia (2020 edition). The results are recorded below.

| Description | Time required for the complete dissolution of the lump after the addition of normal saline |
|---|---|
| Slow reconstitution rate | Reconstitution time ≥ 15 sec |

-continued

| | |
|---|---|
| Moderate reconstitution rate | 5 sec ≤ Reconstitution time < 15 sec |
| Fast reconstitution rate | Reconstitution time < 5 sec |

| Example | Sample retention temperature (6 months) | Reconstitution rate and reconstituted solution property |
|---|---|---|
| 1 | 5° C. | Slow reconstitution rate, with a small number of visible particles observed with naked eyes |
| | 25° C. | Slow reconstitution rate, with a small number of visible particles observed with naked eyes |
| | 40° C. | Moderate reconstitution rate, with a small number of visible particles observed with naked eyes |
| 2 | 5° C. | Slow reconstitution rate, with a small number of visible particles observed with naked eyes |
| | 25° C. | Slow reconstitution rate, with a small number of visible particles observed with naked eyes |
| | 40° C. | Moderate reconstitution rate, with no visible particle and a small number of insoluble particles on the filter membrane after filtration observed under a microscope |
| 3 | 5° C. | Moderate reconstitution rate, with no visible particle and no insoluble particle on the filter membrane after filtration observed under a microscope |
| | 25° C. | Fast reconstitution rate, with no visible particle and no insoluble particle on the filter membrane after filtration observed under a microscope |
| | 40° C. | Fast reconstitution rate, with no visible particle and no insoluble particle on the filter membrane after filtration observed under a microscope |
| 4 | 5° C. | Fast reconstitution rate, with no visible particle and no insoluble particle on the filter membrane after filtration observed under a microscope |
| | 25° C. | Fast reconstitution rate, with no visible particle and no insoluble particle on the filter membrane after filtration observed under microscope |
| | 40° C. | Fast reconstitution rate, with no visible particle and no insoluble particle on the filter membrane after filtration observed under a microscope |
| 5 | 5° C. | Fast reconstitution rate, with no visible particle and no insoluble particle on the filter membrane after filtration observed under a microscope |
| | 25° C. | Fast reconstitution rate, with no visible particle and no insoluble particle on the filter membrane after filtration observed under a microscope |
| | 40° C. | Fast reconstitution rate, with no visible particle and no insoluble particle on the filter membrane after filtration observed under a microscope |
| 6 | 5° C. | Fast reconstitution rate, with no visible particle and no insoluble particle on the filter membrane after filtration observed under a microscope |
| | 25° C. | Fast reconstitution rate, with no visible particle and no insoluble particle on the filter membrane after filtration observed under a microscope |
| | 40° C. | Fast reconstitution rate, with no visible particle and no insoluble particle on the filter membrane after filtration observed under a microscope |

The results show that the addition of an appropriate amount of meglumine (≥0.5%) in the formulation was beneficial to the reconstitution of the preparation and the improvement of the stability and safety of the preparation in clinical use.

II. Examination of isomer changes of long-term sample retention

Several samples of each example were stored in constant temperature and humidity boxes at 5° C., 25° C. and 40° C. respectively. One bottle of samples of each example was taken out respectively under each sample retention condition after 1 month, 3 months and 6 months for isomer detection. The content of (S)-ketorolac was recorded below.

| Example | Sample retention condition | (S)-ketorolac after 1 month (%) | (S)-ketorolac after 3 months (%) | (S)-ketorolac after 6 months (%) |
|---|---|---|---|---|
| 1 | 5° C. | 98.76 | 98.65 | 98.51 |
| | 25° C. | 98.47 | 98.40 | 98.26 |
| | 40° C. | 98.26 | 98.19 | 98.04 |
| 2 | 5° C. | 98.79 | 98.58 | 98.47 |
| | 25° C. | 98.50 | 98.35 | 98.18 |
| | 40° C. | 98.17 | 98.21 | 97.96 |

-continued

| Example | Sample retention condition | (S)-ketorolac after 1 month (%) | (S)-ketorolac after 3 months (%) | (S)-ketorolac after 6 months (%) |
|---|---|---|---|---|
| 3 | 5° C. | 98.82 | 98.74 | 98.61 |
| | 25° C. | 98.55 | 98.39 | 98.14 |
| | 40° C. | 98.31 | 98.32 | 98.10 |
| 4 | 5° C. | 98.85 | 98.70 | 98.72 |
| | 25° C. | 98.55 | 98.44 | 98.34 |
| | 40° C. | 98.38 | 98.28 | 98.19 |
| 5 | 5° C. | 98.20 | 98.04 | 97.95 |
| | 25° C. | 97.84 | 97.67 | 97.33 |
| | 40° C. | 97.66 | 97.42 | 97.12 |
| 6 | 5° C. | 98.01 | 97.84 | 97.78 |
| | 25° C. | 97.65 | 97.43 | 97.36 |
| | 40° C. | 97.29 | 97.12 | 96.85 |

The results show that the racemization of (S)-ketorolac increased with the increase of the dosage of meglumine in each example under respective sample retention condition, and the preferred dosage of meglumine should be less than or equal to 1% for the sake of the optical stability of the raw materials.

Examples 1 to 12 below further describe the present application and all can achieve the effects described in the above-mentioned test examples, but these examples are only intended to illustrate the present application and are not intended to limit the present application.

Example 1 Preparation of Lyophilized Powder Injection of (S)-ketorolac Sodium Salt Formulation:

(S)-ketorolac sodium salt: 1.1 g;

mannitol: 11 g;

anhydrous disodium hydrogen phosphate: 1.44 g;

5% sodium dihydrogen phosphate solution: appropriate amount, adjusting pH to be 6.8; and water for injection: supplementing the solution to the total amount of 200 g.

Preparation method:

Step 1: According to the above formulation, mannitol and anhydrous disodium hydrogen phosphate were dissolved with 70% to 80% water for injection to obtain a clear solution, (S)-ketorolac sodium salt was added and stirred for dissolution, the pH was adjusted to 6.8 with 5% sodium dihydrogen phosphate solution, and the solution was supplemented to the constant volume total amount with water for injection.

Step 2: The drug liquid was subjected to aseptic filtration sequentially through polyethersulfone material filter elements with pore diameters of 0.45 0.22 1.tm and 0.22 and quality control was performed on the content of the intermediate solution; the drug liquid was packed in a neutral borosilicate glass tube injection bottle; after stoppered partially, the drug liquid was pre-frozen at −5° C. to −10° C. for 2 hours, cooled to −40° C. and kept for 3 hours, heated to —20° C. to 0° C., subjected to sublimation drying for 8 hours to 12 hours, then heated to 10° C. to 20° C., subjected to vacuum drying for 6 hours to 12 hours, then stoppered completely, removed out of the cabinet, and finally capped to give the lyophilized powder injection product of (S)-ketorolac sodium salt. The relevant detection data are below.

| Detection item | | Content (%) |
|---|---|---|
| Isomer | Day 0 | 0.13 |
| ((R)-ketorolac) % | 6 months at 25° C. | 0.58 |
| Moisture % | Day 0 | 1.34 |

Example 2 Preparation of Lyophilized Powder Injection of (S)-ketorolac Tromethamine Salt Formulation:

(S)-ketorolac tromethamine salt: 1.5 g;

mannitol: 10 g;

sodium dihydrogen phosphate dodecahydrate: 1.44 g;

0.5 mol/L sodium dihydrogen phosphate solution: appropriate amount, adjusting pH to be 6.5; and water for injection: supplementing the solution to the total amount of 200 g.

Preparation method:

Step 1: According to the above formulation, mannitol and sodium dihydrogen phosphate dodecahydrate were dissolved with 70% to 80% water for injection to obtain a clear solution, (S)-ketorolac tromethamine salt was added and stirred for dissolution, the pH was adjusted to 6.5 with 5 mol/L sodium dihydrogen phosphate solution, and the solution was supplemented to the constant volume total amount with water for injection.

Step 2: The drug liquid was subjected to aseptic filtration sequentially through polyethersulfone material filter elements with pore diameters of 0.45 0.22 1.tm and 0.22 and quality control was performed on the content of the intermediate solution; the drug liquid was packed in a neutral borosilicate glass tube injection bottle; after stoppered partially, the drug liquid was pre-frozen at −5° C. to −10° C. for 2 hours, cooled to −40° C. and kept for 3 hours, heated to −20° C. to 0° C., subjected to sublimation drying for 8 hours to 12 hours, then heated to 10° C. to 20° C., subjected to vacuum drying for 6 hours to 12 hours, then stoppered completely, removed out of the cabinet, and finally capped to give the lyophilized powder injection product of (S)-ketorolac tromethamine salt. The relevant detection data are below.

| Detection item | | Content (%) |
|---|---|---|
| Isomer | Day 0 | 0.50 |
| ((R)-ketorolac) % | 6 months at 25° C. | 0.85 |
| Moisture % | Day 0 | 1.11 |

Example 3 Preparation of Lyophilized Powder Injection of (S)-ketorolac Arginine Salt Formulation:

(S)-ketorolac arginine salt: 1.7 g;

mannitol: 14 g;

sodium citrate: 1.5 g;

0.5 mol/L citric acid solution: appropriate amount, adjusting pH to be 7.0; and water for injection: supplementing the solution to the total amount of 200 g.

Preparation method:

Step 1: According to the above formulation, mannitol and sodium citrate were dissolved with 70% to 80% water for injection to obtain a clear solution, (S)-ketorolac arginine salt was added and stirred for dissolution, the pH was adjusted to 7.0 with 0.5 mol/L citric acid solution, and the solution was supplemented to the constant volume total amount with water for injection.

Step 2: The drug liquid was subjected to aseptic filtration sequentially through polyethersulfone material filter elements with pore diameters of 0.45 μm, 0.22 μm and 0.22 and quality control was performed on the content of the intermediate solution; the drug liquid was packed in a neutral borosilicate glass tube injection bottle; after stoppered partially, the drug liquid was pre-frozen at −5° C. to −10° C. for 2 hours, cooled to −40° C. and kept for 3 hours, heated to —20° C. to 0° C., subjected to sublimation drying for 8 hours to 12 hours, then heated to 10° C. to 20° C., subjected to vacuum drying for 6 hours to 12 hours, then stoppered completely, removed out of the cabinet, and finally capped to give the lyophilized powder injection product of (S)-ketorolac arginine salt. The relevant detection data are below.

| Detection item | | Content (%) |
|---|---|---|
| Isomer | Day 0 | 0.50 |
| ((R)-ketorolac) % | 6 months at 25° C. | 0.75 |
| Moisture % | Day 0 | 1.20 |

Example 4 Preparation of Lyophilized Powder Injection of (S)-ketorolac

Formulation:

(S)-ketorolac: 1.0 g;

mannitol: 10 g;

disodium edetate: 0.1 g;

sodium dihydrogen phosphate dodecahydrate: 3.60 g;

0.5 mol/L disodium hydrogen phosphate solution: appropriate amount, adjusting pH to be 7.2; and water for injection: supplementing the solution to the total amount of 200 g.

Preparation method:

Step 1: According to the above formulation, mannitol, sodium dihydrogen phosphate dodecahydrate and disodium edetate were dissolved with 70% to 80% water for injection to obtain a clear solution, (S)-ketorolac was added and stirred for dissolution, the pH was adjusted to 7.2 with 0.5 mol/L disodium hydrogen phosphate solution, and the solution was supplemented to the constant volume total amount with water for injection.

Step 2: The drug liquid was subjected to aseptic filtration sequentially through polyethersulfone material filter elements with pore diameters of 0.45 μm, 0.22 μm and 0.22 μm, and quality control was performed on the content of the intermediate solution; the drug liquid was packed in a neutral borosilicate glass tube injection bottle; after stoppered partially, the drug liquid was pre-frozen at −5° C. to −10° C. for 2 hours, cooled to −40° C. and kept for 3 hours, heated to —20° C. to 0° C., subjected to sublimation drying for 8 hours to 12 hours, then heated to 10° C. to 20° C., subjected to vacuum drying for 6 hours to 12 hours, then stoppered completely, removed out of the cabinet, and finally capped to give the lyophilized powder injection product of (S)-ketorolac. The relevant detection data are below.

| Time point | Property | (R)-ketorolac (%) | Inspection of visible particles and insoluble particles in the reconstituted solution |
|---|---|---|---|
| Day 0 | White lump | 0.61 | Qualified |
| 1 month at 5° C. | White lump | 0.62 | Qualified |
| 2 months at 5° C. | White lump | 0.65 | Qualified |
| 3 months at 5° C. | White lump | 0.64 | Unqualified, with a small number of visible particles |
| 6 months at 5° C. | White lump | 0.64 | Unqualified, with a small number of visible particles |
| 1 month at 25° C. | White lump | 0.67 | Qualified |
| 2 months at 25° C. | White lump | 0.70 | Qualified |
| 3 months at 25° C. | White lump | 0.79 | Unqualified, with a small number of visible particles |
| 6 months at 25° C. | White lump | 0.86 | Unqualified, with a small number of visible particles |
| 1 month at 40° C. | White lump | 1.03 | Qualified |
| 2 months at 40° C. | White lump | 1.20 | Qualified |
| 3 months at 40° C. | White lump | 1.40 | Qualified |
| 6 months at 40° C. | White lump | 1.53 | Unqualified, with a small number of visible particles |

Example 5 Preparation of Lyophilized Powder Injection of (S)-ketorolac

Formulation:

(S)-ketorolac: 1.0 g;

mannitol: 10 g;

meglumine: 2.0 g;

sodium dihydrogen phosphate dodecahydrate: 3.64 g;

0.5 mol/L disodium hydrogen phosphate solution: appropriate amount, adjusting pH to be 7.0; and water for injection: supplementing the solution to the total amount of 200 g.

Preparation method:

Step 1: According to the above formulation, mannitol, sodium dihydrogen phosphate dodecahydrate and meglumine were dissolved with 70% to 80% water for injection to obtain a clear solution, (S)-ketorolac was added and stirred for dissolution, the pH was adjusted to 7.0 with 0.5 mol/L disodium hydrogen phosphate solution, and the solution was supplemented to the constant volume total amount with water for injection.

Step 2: The drug liquid was subjected to aseptic filtration sequentially through polyethersulfone material filter elements with pore diameters of 0.45 μm, 0.22 μm and 0.22 μm, and quality control was performed on the content of the intermediate solution; the drug liquid was packed in a neutral borosilicate glass tube injection bottle; after stoppered partially, the drug liquid was pre-frozen at −5° C. to −10° C. for 2 hours, cooled to −40° C. and kept for 3 hours, heated to −20° C. to 0° C., subjected to sublimation drying for 8 hours to 12 hours, then heated to 10° C. to 20° C., subjected to vacuum drying for 6 hours to 12 hours, then stoppered completely, removed out of the cabinet, and finally capped to give the lyophilized powder injection product of (S)-ketorolac. The relevant detection data are below.

| Time point | Property | (R)-ketorolac (%) | Inspection of visible particles and insoluble particles in the reconstituted solution |
|---|---|---|---|
| Day 0 | White lump | 0.42 | Qualified |
| 1 month at 5° C. | White lump | 0.42 | Qualified |
| 2 months at 5° C. | White lump | 0.42 | Qualified |
| 3 months at 5° C. | White lump | 0.43 | Qualified |
| 6 months at 5° C. | White lump | 0.43 | Qualified |
| 1 month at 25° C. | White lump | 0.41 | Qualified |
| 2 months at 25° C. | White lump | 0.46 | Qualified |
| 3 months at 25° C. | White lump | 0.48 | Qualified |
| 6 months at 25° C. | White lump | 0.58 | Qualified |
| 1 month at 40° C. | White lump | 0.73 | Qualified |
| 2 months at 40° C. | White lump | 0.91 | Qualified |
| 3 months at 40° C. | White lump | 1.00 | Qualified |
| 6 months at 40° C. | White lump | 1.32 | Qualified |

Example 6 Preparation of Lyophilized Powder Injection of (S)-ketorolac Tromethamine Salt Formulation:

(S)-ketorolac tromethamine salt: 3.0 g;

mannitol: 15 g;

sodium calcium edetate: 0.2 g;

sodium acetate: 3.64 g;

0.5 mol/L acetic acid solution: appropriate amount, adjusting pH to be 6.9; and water for injection: supplementing the solution to the total amount of 200 g.

Preparation method:

Step 1: According to the above formulation, mannitol, sodium dihydrogen phosphate dodecahydrate and meglumine were dissolved with 70% to 80% water for injection to obtain a clear solution, (S)-ketorolac was added and stirred for dissolution, the pH was adjusted to 7.0 with 0.5 mol/L disodium hydrogen phosphate solution, and the solution was supplemented to the constant volume total amount with water for injection.

Step 2: The drug liquid was subjected to aseptic filtration sequentially through polyethersulfone material filter elements with pore diameters of 0.45 μm, 0.22 μm and 0.22 μm, and quality control was performed on the content of the intermediate solution; the drug liquid was packed in a neutral borosilicate glass tube injection bottle; after stoppered partially, the drug liquid was pre-frozen at −5° C. to −10° C. for 2 hours, cooled to −40° C. and kept for 3 hours, heated to −20° C. to 0° C., subjected to sublimation drying for 8 hours to 12 hours, then heated to 10° C. to 20° C., subjected to vacuum drying for 6 hours to 12 hours, then stoppered completely, removed out of the cabinet, and finally capped to give the lyophilized powder injection product of (S)-ketorolac. The relevant detection data are below.

| Time point | Property | (R)-ketorolac (%) | Inspection of visible particles and insoluble particles in the reconstituted solution |
|---|---|---|---|
| Day 0 | White lump | 0.53 | Qualified |
| 1 month at 5° C. | White lump | 0.53 | Qualified |
| 2 months at 5° C. | White lump | 0.53 | Qualified |
| 3 months at 5° C. | White lump | 0.55 | Qualified |
| 6 months at 5° C. | White lump | 0.56 | Qualified |
| 1 month at 25° C. | White lump | 0.58 | Qualified |
| 2 months at 25° C. | White lump | 0.61 | Qualified |
| 3 months at 25° C. | White lump | 0.69 | Qualified |
| 6 months at 25° C. | White lump | 0.75 | Qualified |
| 1 month at 40° C. | White lump | 0.72 | Qualified |
| 2 months at 40° C. | White lump | 0.96 | Qualified |
| 3 months at 40° C. | White lump | 1.05 | Qualified |
| 6 months at 40° C. | White lump | 1.43 | Qualified |

Example 7 Preparation of Lyophilized Powder Injection of (S)-ketorolac Arginine Salt Formulation:

(S)-ketorolac arginine salt: 2.0 g;

maltodextrin: 13 g;

sodium bisulfite: 0.2 g;

sodium phosphate: 3.1g;

0.5 mol/L phosphoric acid solution: appropriate amount, adjusting pH to be 7.1; and water for injection: supplementing the solution to the total amount of 200 g.

Preparation method:

Step 1: According to the above formulation, maltodextrin, sodium phosphate and sodium bisulfite were dissolved with 70% to 80% water for injection to obtain a clear solution, (S)-ketorolac arginine salt was added and stirred for dissolution, the pH was adjusted to 7.0 with 0.5 mol/L phosphoric acid solution, and the solution was supplemented to the constant volume total amount with water for injection.

Step 2: The drug liquid was subjected to aseptic filtration sequentially through polyethersulfone material filter elements with pore diameters of 0.45 μm, 0.22 μm and 0.22 μm, and quality control was performed on the content of the intermediate solution; the drug liquid was packed in a neutral borosilicate glass tube injection bottle; after stoppered partially, the drug liquid was pre-frozen at −5° C. to −10° C. for 2 hours, cooled to −40° C. and kept for 3 hours, heated to −20° C. to 0° C., subjected to sublimation drying for 8 hours to 12 hours, then heated to 10° C. to 20° C., subjected to vacuum drying for 6 hours to 12 hours, then stoppered completely, removed out of the cabinet, and finally capped to give the lyophilized powder injection product of (S)-ketorolac arginine salt. The relevant detection data are below.

| Time point | Property | (R)-ketorolac (%) | Inspection of visible particles and insoluble particles in reconstituted solution |
|---|---|---|---|
| Day 0 | White lump | 0.67 | Qualified |
| 1 month at 5° C. | White lump | 0.67 | Qualified |
| 2 months at 5° C. | White lump | 0.68 | Qualified |
| 3 months at 5° C. | White lump | 0.69 | Qualified |
| 6 months at 5° C. | White lump | 0.72 | Qualified |
| 1 month at 25° C. | White lump | 0.69 | Qualified |
| 2 months at 25° C. | White lump | 0.73 | Qualified |
| 3 months at 25° C. | White lump | 0.80 | Qualified |
| 6 months at 25° C. | White lump | 0.88 | Qualified |
| 1 month at 40° C. | White lump | 0.73 | Qualified |
| 2 months at 40° C. | White lump | 0.96 | Qualified |
| 3 months at 40° C. | White lump | 1.2 | Qualified |
| 6 months at 40° C. | White lump | 1.62 | Qualified |

Example 8 Preparation of Lyophilized Powder Injection of (S)-ketorolac

Formulation:

(S)-ketorolac: 1.0 g;

mannitol: 10 g;

meglumine: 1.5 g;

vitamin C: 0.5 g;

sodium dihydrogen phosphate dodecahydrate: 3.64 g;

0.5 mol/L disodium hydrogen phosphate solution: appropriate amount, adjusting pH to be 7.0; and water for injection: supplementing the solution to the total amount of 200 g.

Preparation method:

Step 1: According to the above formulation, mannitol, sodium dihydrogen phosphate dodecahydrate, meglumine and vitamin C were dissolved with 70% to 80% water for injection to obtain a clear solution, (S)-ketorolac was added and stirred for dissolution, the pH was adjusted to 7.0 with 0.5 mol/L disodium hydrogen phosphate solution, and the solution was supplemented to the constant volume total amount with water for injection.

Step 2: The drug liquid was subjected to aseptic filtration sequentially through polyethersulfone material filter elements with pore diameters of 0.45 μm, 0.22 μm and 0.22 μm, and quality control was performed on the content of the intermediate solution; the drug liquid was packed in a neutral borosilicate glass tube injection bottle; after stoppered partially, the drug liquid was pre-frozen at −5° C. to −10° C. for 2 hours, cooled to −40° C. and kept for 3 hours, heated to −20° C. to 0° C., subjected to sublimation drying for 8 hours to 12 hours, then heated to 10° C. to 20° C., subjected to vacuum drying for 6 hours to 12 hours, then stoppered completely, removed out of the cabinet, and finally capped to give the lyophilized powder injection product of (S)-ketorolac. The relevant detection data are below.

| Time point | Property | (R)-ketorolac (%) | Total amount of impurities 1-hydroxy ketorolac and 1-keto ketorolac (%) |
|---|---|---|---|
| Day 0 | White lump | 0.40 | 0.18 |
| 6 months at 5° C. | White lump | 0.45 | 0.20 |
| 6 months at 25° C. | White lump | 0.69 | 0.25 |
| 6 months at 40° C. | White lump | 1.36 | 0.29 |

Example 9 Preparation of Lyophilized Powder Injection of (S)-ketorolac Tromethamine Salt Formulation:

(S)-ketorolac tromethamine salt: 1.8 g;

mannitol: 12 g;

arginine: 0.9 g;

L-cysteine: 0.2 g;

citric acid: 0.8 g;

0.5 mol/L sodium citrate solution: appropriate amount, adjusting pH to be 7.2; and water for injection: supplementing the solution to the total amount of 200 g.

Preparation method:

Step 1: According to the above formulation, mannitol, arginine, L-cysteine and citric acid were dissolved with 70% to 80% water for injection to obtain a clear solution, (S)-ketorolac tromethamine salt was added and stirred for dissolution, the pH was adjusted to 7.2 with 0.5 mol/L sodium citrate solution, and the solution was supplemented to the constant volume total amount with water for injection.

Step 2: The drug liquid was subjected to aseptic filtration sequentially through polyethersulfone material filter elements with pore diameters of 0.45 μm, 0.22 μm and 0.22 μm, and quality control was performed on the content of the intermediate solution; the drug liquid was packed in a neutral borosilicate glass tube injection bottle; after stoppered partially, the drug liquid was pre-frozen at −5° C. to −10° C. for 2 hours, cooled to −40° C. and kept for 3 hours, heated to −20° C. to 0° C., subjected to sublimation drying for 8 hours to 12 hours, then heated to 10° C. to 20° C., subjected to vacuum drying for 6 hours to 12 hours, then stoppered completely, removed out of the cabinet, and finally capped to give the lyophilized powder injection product of (S)-ketorolac tromethamine salt. The relevant detection data are below.

| Time point | Property | (R)-ketorolac (%) | Total amount of impurities 1-hydroxy ketorolac and 1-keto ketorolac (%) |
|---|---|---|---|
| Day 0 | White lump | 0.50 | 0.15 |
| 6 months at 5° C. | White lump | 0.54 | 0.19 |
| 6 months at 25° C. | White lump | 0.71 | 0.23 |
| 6 months at 40° C. | White lump | 1.44 | 0.27 |

Example 10 Preparation of Lyophilized Powder Injection of (S)-ketorolac

Formulation:
(S)-ketorolac: 2.0 g;
mannitol: 20 g;
meglumine: 2.0 g;
sodium dihydrogen phosphate dodecahydrate: 7.22 g;
5 0.5 mol/L disodium hydrogen phosphate solution: appropriate amount, adjusting pH to be 6.9 to 7.0; and
water for injection: supplementing the solution to the total amount of 400 g.

Preparation method:

Step 1: According to the above formulation, mannitol, sodium dihydrogen phosphate dodecahydrate and meglumine were dissolved with 70% to 80% water for injection to obtain a clear solution, (S)-ketorolac was added and stirred for dissolution, the pH was adjusted to 7.0 with 0.5 mol/L disodium hydrogen phosphate solution, and the solution was supplemented to the constant volume total amount with water for injection.

Step 2: The drug liquid was subjected to aseptic filtration sequentially through polyethersulfone material filter elements with pore diameters of 0.45 μm, 0.22 μm and 0.22 μm, and quality control was performed on the content of the intermediate solution; the drug liquid was packed in a neutral borosilicate glass tube injection bottle; after stoppered partially, the drug liquid was pre-frozen at −5° C. to −10° C. for 2 hours, cooled to −40° C. and kept for 3 hours, heated to −20° C. to 0° C., subjected to sublimation drying for 8 hours to 12 hours, then heated to 10° C. to 20° C., subjected to vacuum drying for 6 hours to 12 hours, then stoppered completely, removed out of the cabinet, and finally capped to give the lyophilized powder injection product of (S)-ketorolac.

Example 11 Preparation of Lyophilized Powder Injection of (S)-ketorolac

Formulation:
(S)-ketorolac: 2.0 g;
mannitol: 20 g;
arginine: 2.0 g;
sodium dihydrogen phosphate dodecahydrate: 7.23 g;
0.5 mol/L disodium hydrogen phosphate solution: appropriate amount, adjusting pH to be 7.0 to 7.1; and
water for injection: supplementing the solution to the total amount of 400 g.

Preparation method:

Step 1: According to the above formulation, mannitol, sodium dihydrogen phosphate dodecahydrate and arginine were dissolved with 70% to 80% water for injection to obtain a clear solution, (S)-ketorolac was added and stirred for dissolution, the pH was adjusted to 7.0 with 0.5 mol/L disodium hydrogen phosphate solution, and the solution was supplemented to the constant volume total amount with water for injection.

Step 2: The drug liquid was subjected to aseptic filtration sequentially through polyethersulfone material filter elements with pore diameters of 0.45 μm, 0.22 μm and 0.22 μm, and quality control was performed on the content of the intermediate solution; the drug liquid was packed in a neutral borosilicate glass tube injection bottle; after stoppered partially, the drug liquid was pre-frozen at −5° C. to −10° C. for 2 hours, cooled to −40° C. and kept for 3 hours, heated to −20° C. to 0° C., subjected to sublimation drying for 8 hours to 12 hours, then heated to 10° C. to 20° C., subjected to vacuum drying for 6 hours to 12 hours, then stoppered completely, removed out of the cabinet, and finally capped to give the lyophilized powder injection product of (S)-ketorolac.

Example 12 Pharmacokinetic testing in beagle dogs and cynomolgus monkeys after single administration Representative batches of lyophilized powder injection of (S)-ketorolac described in the present application were selected to examine the drug metabolism in vivo of beagle dogs and cynomolgus monkeys. The mode of administration was single intravenous administration. The concentration of (S)-ketorolac and (R)-ketorolac in plasma samples was measured by LC-MS/MS, and the blood drug concentration-time curve was plotted to obtain the main pharmacokinetic parameters and examine the chiral transformation of (S)-ketorolac and (R)-ketorolac in animals. The data are summarized below.

Pharmacokinetic parameters after single intravenous administration of different doses of (S)-ketorolac in male and female beagle dogs (mean±standard deviation)

| | | 0.16 mg/kg | | 3.2 mg/kg | |
|---|---|---|---|---|---|
| Parameter | Unit | (S)-ketorolac | (R)-ketorolac | (S)-ketorolac | (R)-ketorolac |
| $AUC_{0-t}$ | h · ng/mL | 545 ± 147 | 11.7 ± 1.21 | 41633 ± 3539 | 724 ± 259 |
| $AUC_{0-\infty}$ | h · ng/mL | 950 ± 385 | 79.2 ± 57.0 | 117433 ± 25934 | NA |
| $MRT_{0-t}$ | h | 1.61 ± 0.400 | 3.07 ± 0.144 | 2.50 ± 0.149 | 3.52 ± 0.33 |
| $t_{1/2}$ | h | 7.13 ± 2.93 | 22.7 ± 16.8 | 10.3 ± 2.18 | NA |
| $V_{ss}$ | mL/kg | 1293 ± 432 | — | 391 ± 34.6 | — |
| CL | mL/h/kg | 193 ± 89.8 | — | 28.3 ± 6.94 | — |
| Chiral transformation rate | % | — | 2.10 | — | 1.71 |

Chiral transformation rate (%) = $(AUC_{0-t})_R/[(AUC_{0-t})_S + (AUC_{0-t})_R] \times 100$
NA: Not Available Pharmacokinetic parameters after single intravenous administration of different doses of (S)-ketorolac tromethamine salt in male and female cynomolgus monkeys (mean±standard deviation)

| Parameter | Unit | 0.24 mg/kg (S)-ketorolac | 0.24 mg/kg (R)-ketorolac | 2.4 mg/kg (S)-ketorolac | 2.4 mg/kg (R)-ketorolac |
|---|---|---|---|---|---|
| $AUC_{0-t}$ | h · ng/mL | 2503 ± 1293 | 143 ± 107 | 24500 ± 8616 | 2233 ± 1382 |
| $AUC_{0-\infty}$ | h · ng/mL | 2900 ± 1532 | 366 ± 327 | 26000 ± 8937 | 4607 ± 3378 |
| $MRT_{0-t}$ | h | 1.73 ± 0.595 | 3.03 ± 0.327 | 1.49 ± 0.39 | 2.84 ± 0.18 |
| $t_{1/2}$ | h | 1.95 ± 0.948 | 4.72 ± 1.32 | 1.53 ± 0.344 | 5.39 ± 1.71 |
| $V_{ss}$ | mL/kg | 224 ± 77.8 | — | 180 ± 38.1 | — |
| CL | mL/h/kg | 106 ± 67.4 | — | 102 ± 40.8 | — |
| Chiral transformation rate | % | — | 4.98 | — | 8.35 |

Chiral transformation rate (%) = $(AUC_{0-t})_R/[(AUC_{0-t})_S + (AUC_{0-t})_R] \times 100$ The results showed that the conversion rate of (S)-ketorolac to (R)-ketorolac was low in beagle dogs and cynomolgus monkeys, which was close to the conversion rate of 6.5% in human reported in the literature (J Cln Pharmacol 1996; 36: 521-539). Under the condition of high dosage, the conversion rate of (S)-ketorolac to racemization did not significantly increase, indicating that the (S)-ketorolac lyophilized powder injection described in the present application could still maintain a high proportion of (S)-ketorolac after being injected into animals intravenously, which laid a good foundation for efficient exertion of analgesic effect.

What is claimed is:

1. A pharmaceutical composition of (S)-ketorolac, comprising:

(1) (S)-ketorolac, (S)-ketorolac tromethamine salt or (S)-ketorolac arginine salt;

(2) a pH-adjusting agent comprising a buffer and a pH-adjusting agent component selected from the group consisting of: sodium hydroxide, potassium hydroxide, tromethamine, triethanolamine, diethanolamine, ethanolamine, sodium citrate, potassium citrate, sodium carbonate, sodium bicarbonate, anhydrous or crystalline hydrate of disodium hydrogen phosphate, anhydrous or crystalline hydrate of sodium dihydrogen phosphate, anhydrous or crystalline hydrate of dipotassium hydrogen phosphate, anhydrous or crystalline hydrate of potassium dihydrogen phosphate, sodium phosphate, phosphoric acid, hydrochloric acid, tartaric acid, and lactic acid, wherein the buffer is anhydrous or crystalline water-containing phosphate and a solution thereof, wherein the anhydrous or crystalline water-containing phosphate is selected from the group consisting of sodium dihydrogen phosphate, disodium hydrogen phosphate, potassium dihydrogen phosphate, dipotassium hydrogen phosphate, sodium phosphate, tripotassium phosphate, sodium hydrogen phosphate, potassium hydrogen phosphate, ammonium hydrogen phosphate, ammonium dihydrogen phosphate, ammonium phosphate, calcium dihydrogen phosphate, calcium hydrogen phosphate, and zinc phosphate and combinations thereof;

(3) a stabilizer, wherein the stabilizer is selected from one or more of meglumine, and arginine; and (4) a pharmaceutically acceptable excipient selected from mannitol and maltodextrin.

2. The pharmaceutical composition according to claim 1, wherein the pharmaceutical composition is in a dosage form of lyophilized powder injection, solution injection, or sterile powder in which various components are uniformly mixed.

3. The pharmaceutical composition according to claim 2, wherein the dosage form is lyophilized powder injection, and the lyophilized powder injection has optical purity of an active ingredient greater than or equal to 95% after being stored under long-term stability test conditions for 6 months and optical purity of an active ingredient greater than or equal to 90% after being stored under accelerated stability test conditions for 6 months; and a moisture content of the lyophilized powder injection is less than or equal to 5%.

4. The pharmaceutical composition according to claim 3, wherein the pH-adjusting agent component is selected from the group consisting of: anhydrous or crystalline hydrate of disodium hydrogen phosphate, anhydrous or crystalline hydrate of sodium dihydrogen phosphate, phosphoric acid, or an aqueous solution prepared from the same.

5. The pharmaceutical composition according to claim 4, wherein the pH-adjusting agent component is used for regulating a pH value of a lyophilized stock solution when the lyophilized powder injection is prepared to be 6.5 to 7.5.

6. The pharmaceutical composition according to claim 4, wherein a drug concentration of (S)-ketorolac $C_{15}H_{13}NO_3$ in the lyophilized stock solution when the lyophilized powder injection is prepared is 2 mg/ml to 30 mg/ml.

7. The pharmaceutical composition according to claim 4, wherein the lyophilized powder injection is diluted with a clinically commonly used diluent for use, wherein the diluent is selected from 5% glucose injection, 10% glucose injection, glucose sodium chloride injection, 0.9% sodium chloride injection, compound sodium chloride injection, sodium lactate Ringer's injection, compound glucose sodium lactate injection, sterilized water for injection, xylitol injection or fructose injection; and a concentration of (S)-ketorolac $C_{15}H_{13}NO_3$ is 0.05 mg/ml to 5 mg/ml after dilution.

8. The pharmaceutical composition according to claim 4, wherein in the lyophilized powder injection, an active pharmaceutical ingredient is selected from (S)-ketorolac, (S)-ketorolac tromethamine salt or (S)-ketorolac arginine salt; in the pH-adjusting agent, the buffer is selected from anhydrous or crystalline water-containing phosphate;

the excipient is selected from mannitol; and the drug concentration of (S)-ketorolac in the lyophilized stock solution when the lyophilized powder injection is prepared is 5 mg/ml to 7.5 mg/ml, and a pH value of the lyophilized stock solution before lyophilizing is 6.8 to 7.2.

9. The pharmaceutical composition according to claim 8, wherein a molar concentration of phosphate used as the pH-adjusting agent in the lyophilized powder injection is 0.01 mmol/ml to 0.1 mmol/ml; a molar ratio of (S)-ketorolac to phosphate in the lyophilized stock solution is 1:1 to 1:3; and a mass percentage of the excipient mannitol in the lyophilized stock solution is 3% to 7%.

10. The pharmaceutical composition according to claim 1, wherein a mass percentage of the stabilizer in the composition is 0.1% to 5%.

11. The pharmaceutical composition according to claim 4, wherein the lyophilized powder injection further comprises one or more of a metal ion chelating agent or an antioxidant, wherein the metal ion chelating agent is selected from one or more of disodium edetate, sodium calcium edetate, sodium citrate or citric acid, and a weight percentage of the metal ion chelating agent in the lyophilized stock solution is 0.05% to 1%; and the antioxidant is selected from one or more of sodium thiosulfate, sodium sulfite, sodium metabisulfite, sodium bisulfite, vitamin C or L-cysteine, and a weight percentage of the antioxidant in the lyophilized stock solution is 0.02% to 2%.

12. The pharmaceutical composition according to claim 8, wherein in the lyophilized powder injection, the active pharmaceutical ingredient is (S)-ketorolac; the pH-adjusting agent is anhydrous or crystalline water-containing disodium hydrogen phosphate, or an aqueous solution prepared from the same; and the lyophilized powder injection further comprises a stabilizer meglumine, and a mass percentage of the stabilizer in the lyophilized stock solution is 0.1% to 5%.

13. The pharmaceutical composition according to claim 8, wherein in the lyophilized powder injection, the active pharmaceutical ingredient is (S)-ketorolac; in the pH-adjusting agent, the buffer is sodium phosphate and a sodium dihydrogen phosphate hydrate; and the lyophilized powder injection further comprises a stabilizer arginine, and a mass percentage of the stabilizer in the lyophilized stock solution is 0.1% to 5%.

14. The pharmaceutical composition according to claim 8, wherein in the lyophilized powder injection, the active pharmaceutical ingredient is the (S)-ketorolac tromethamine salt; in the pH-adjusting agent, the buffer is anhydrous or crystalline water dipotassium hydrogen phosphate or anhydrous or crystalline water potassium dihydrogen phosphate; the pH adjusting agent component is sodium bicarbonate, hydrochloric acid, or an aqueous solution prepared from the same; and the lyophilized powder injection further comprises a stabilizer arginine, and a mass percentage of the stabilizer in the lyophilized stock solution is 0.1% to 5%.

15. The pharmaceutical composition according to claim 12, wherein the lyophilized powder injection further comprises a metal ion chelating agent, wherein the metal ion chelating agent is selected from disodium edetate or sodium calcium edetate, and a weight percentage of the metal ion chelating agent in the lyophilized stock solution is 0.05% to 1%.

16. The pharmaceutical composition according to claim 12, wherein the lyophilized powder injection further comprises an antioxidant, wherein the antioxidant is selected from sodium bisulfite or vitamin C, and a weight percentage of the antioxidant in the lyophilized stock solution is 0.02% to 2%.

17. The pharmaceutical composition according to claim 8, wherein feed weight percentages of components in the lyophilized stock solution when the lyophilized powder injection is prepared are as follows:

(S)-ketorolac: 0.5% to 0.7%;

disodium hydrogen phosphate dodecahydrate: 1.8% to 2.0%;

mannitol: 6% to 9%;

disodium edetate: 0.05% to 0.1%;

disodium hydrogen phosphate aqueous solution: appropriate amount, adjusted to a pH value of 6.8 to 7.2; and water for injection: added to 100%;

wherein the lyophilized stock solution is aseptically filtered, packed and lyophilized to obtain the lyophilized powder injection.

18. The pharmaceutical composition according to claim 8, wherein feed weight percentages of components in the lyophilized stock solution when the lyophilized powder injection is prepared are as follows:

(S)-ketorolac: 0.5% to 1%;

disodium hydrogen phosphate dodecahydrate: 1.8% to 2.5%;

mannitol: 5% to 15%;

meglumine: 1% to 2%;

disodium hydrogen phosphate aqueous solution: appropriate amount, adjusted to a pH value of 6.8 to 7.2; and water for injection: added to 100%;

wherein the lyophilized stock solution is aseptically filtered, packed and lyophilized to obtain the lyophilized powder injection.

19. A method for the short-term treatment of acute and severe pain requiring opioid-level analgesics, comprising administering an effective amount of the pharmaceutical composition according to claim 1 to a subject in need thereof.

* * * * *